(12) United States Patent
Ho et al.

(10) Patent No.: US 10,344,257 B2
(45) Date of Patent: Jul. 9, 2019

(54) HORIZONTALLY ROCKED BIOREACTOR SYSTEM

(71) Applicant: Timothy Ray Ho, Atlanta, GA (US)

(72) Inventors: Timothy Ray Ho, Atlanta, GA (US); Lewis Ho, Lawrenceville, GA (US)

(73) Assignee: BIOREACTOR SCIENCES LLC, Lawrenceville, GA (US)

( * ) Notice: Subject to any disclaimer, the term of this patent is extended or adjusted under 35 U.S.C. 154(b) by 261 days.

(21) Appl. No.: 15/217,347

(22) Filed: Jul. 22, 2016

(65) Prior Publication Data

US 2017/0022465 A1    Jan. 26, 2017

Related U.S. Application Data

(60) Provisional application No. 62/267,906, filed on Dec. 16, 2015, provisional application No. 62/196,833, filed on Jul. 24, 2015.

(51) Int. Cl.
| | | |
|---|---|---|
| *C12M 3/00* | (2006.01) | |
| *C12M 1/00* | (2006.01) | |
| *C12M 1/12* | (2006.01) | |
| *C12M 1/36* | (2006.01) | |
| *C12M 3/04* | (2006.01) | |

(52) U.S. Cl.
CPC ............ *C12M 25/18* (2013.01); *C12M 27/10* (2013.01); *C12M 27/20* (2013.01); *C12M 41/48* (2013.01)

(58) Field of Classification Search
CPC ...... C12M 27/20; C12M 27/02; C12M 27/10; C12M 27/16
See application file for complete search history.

(56) References Cited

U.S. PATENT DOCUMENTS

| | | | |
|---|---|---|---|
| 4,373,029 A | | 2/1983 | Nees |
| 4,912,048 A | * | 3/1990 | Smith ............... C12M 23/08 206/219 |
| 5,026,650 A | | 6/1991 | Schwarz et al. |
| 5,437,998 A | | 8/1995 | Schwarz et al. |
| 5,766,949 A | | 6/1998 | Liau |
| 5,955,326 A | | 9/1999 | Bungay, III et al. |
| 6,080,581 A | | 6/2000 | Anderson |
| 6,150,159 A | * | 11/2000 | Fry ..................... C12M 23/08 435/298.2 |
| 6,190,913 B1 | | 2/2001 | Singh |
| 8,602,636 B2 | | 12/2013 | Kauling et al. |
| 2004/0048364 A1 | * | 3/2004 | Trosch ............... C12M 21/02 435/292.1 |
| 2008/0274541 A1 | * | 11/2008 | Selker ............... B01F 3/04248 435/289.1 |

(Continued)

FOREIGN PATENT DOCUMENTS

| | | |
|---|---|---|
| TW | M364709 | 9/2009 |
| WO | WO 2014093444 A1 | 6/2014 |

OTHER PUBLICATIONS

Guozheng Wang, Modified CelliGen-Packed Bed Bioreactor for Hybridoma Cell Cultures, Cytotechnology 9, 1992, p. 41-49, Kluwer Academic Publishers, Netherlands.

*Primary Examiner* — Nathan A Bowers
(74) *Attorney, Agent, or Firm* — Thomas|Horstemeyer, LLP

(57) ABSTRACT

Disclosed herein is an improved rocked bioreactor system used for carrying out cell and tissue cultures.

19 Claims, 18 Drawing Sheets

(56) References Cited

U.S. PATENT DOCUMENTS

| | | | |
|---|---|---|---|
| 2010/0015696 A1* | 1/2010 | Claes | B01F 3/04269 |
| | | | 435/303.3 |
| 2011/0033918 A1 | 2/2011 | Asnaghi et al. | |
| 2011/0263021 A1 | 10/2011 | Stobbe | |
| 2013/0171616 A1 | 7/2013 | Niazi | |
| 2014/0011270 A1* | 1/2014 | Chotteau | C12M 23/14 |
| | | | 435/326 |

* cited by examiner

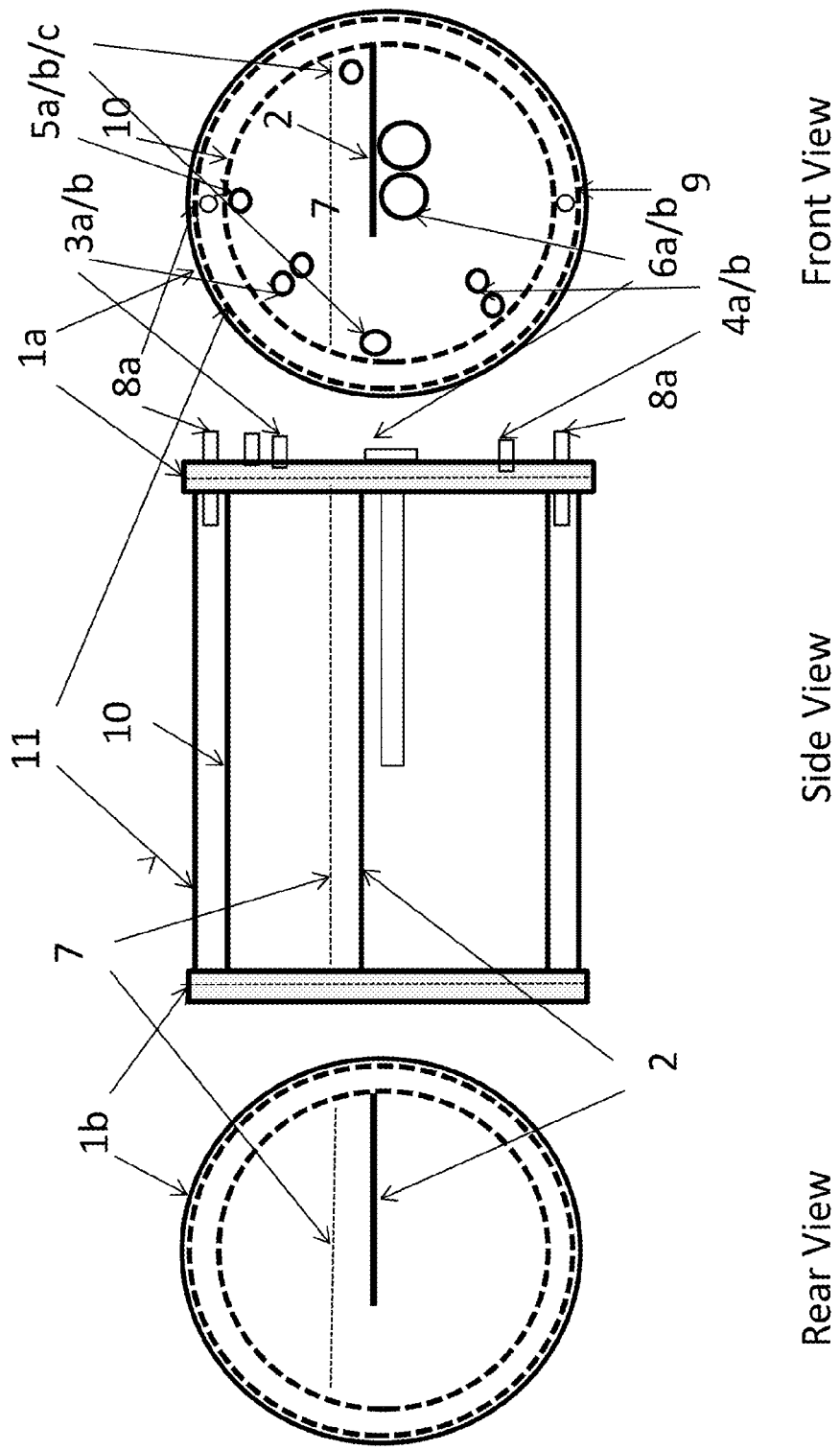

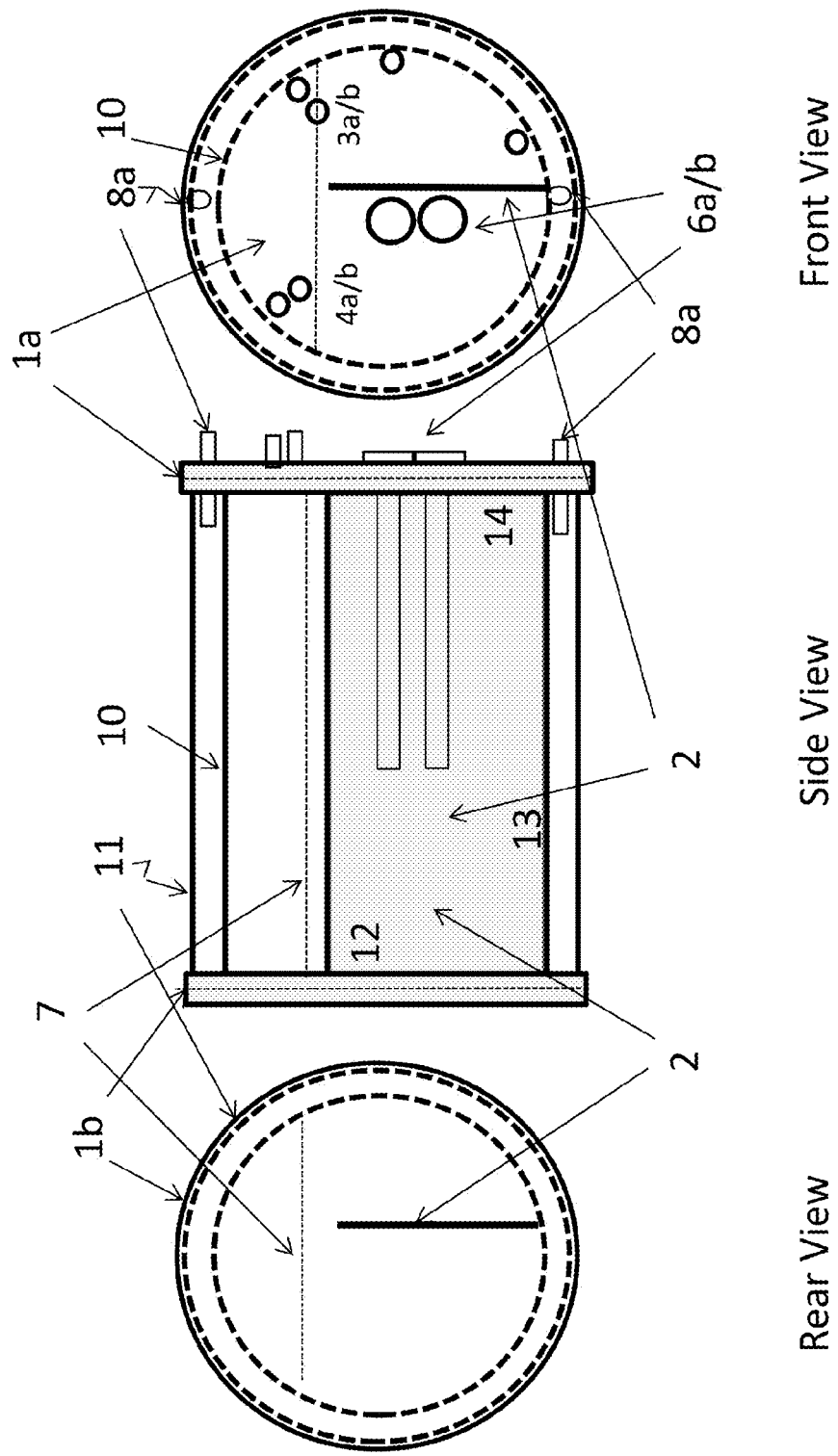
FIG. 1b (RA=90)

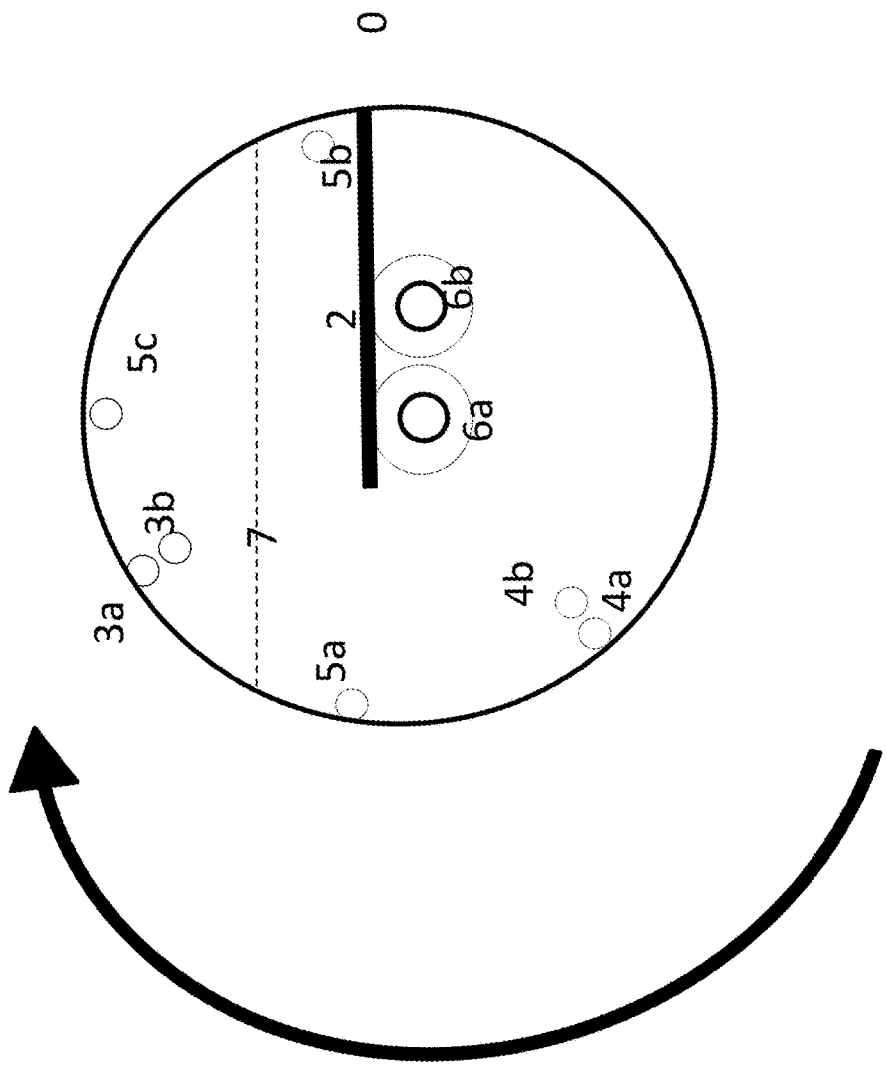

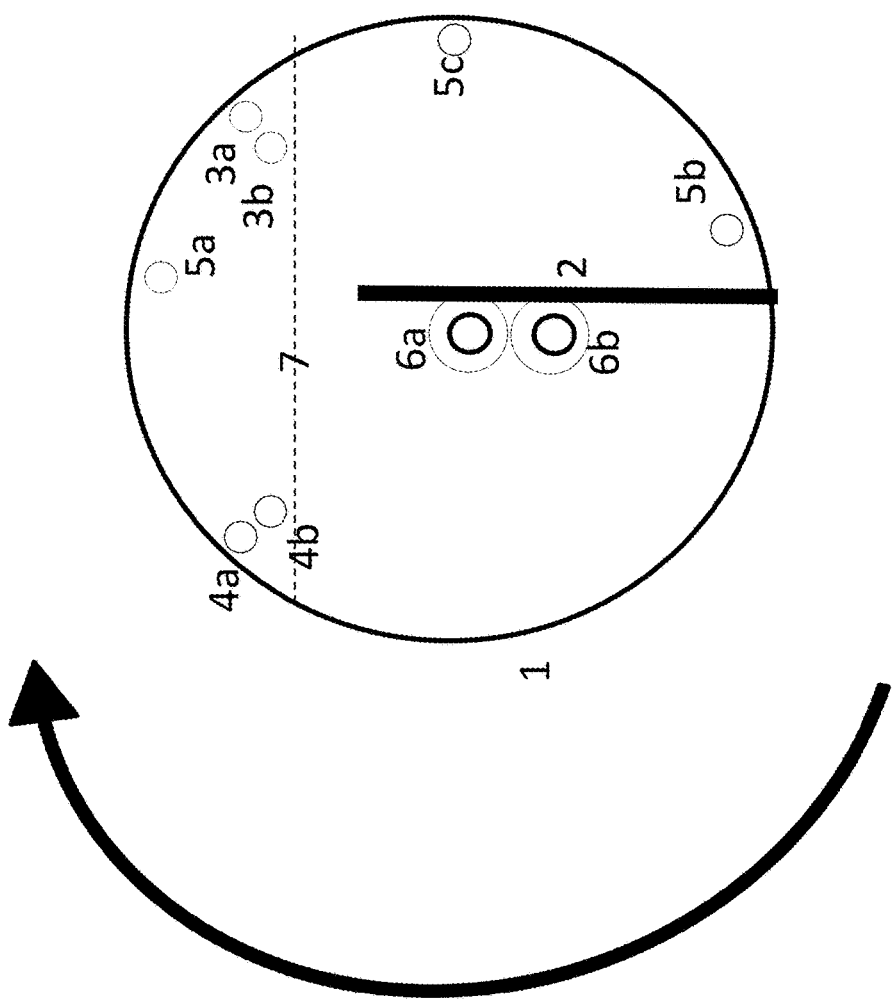

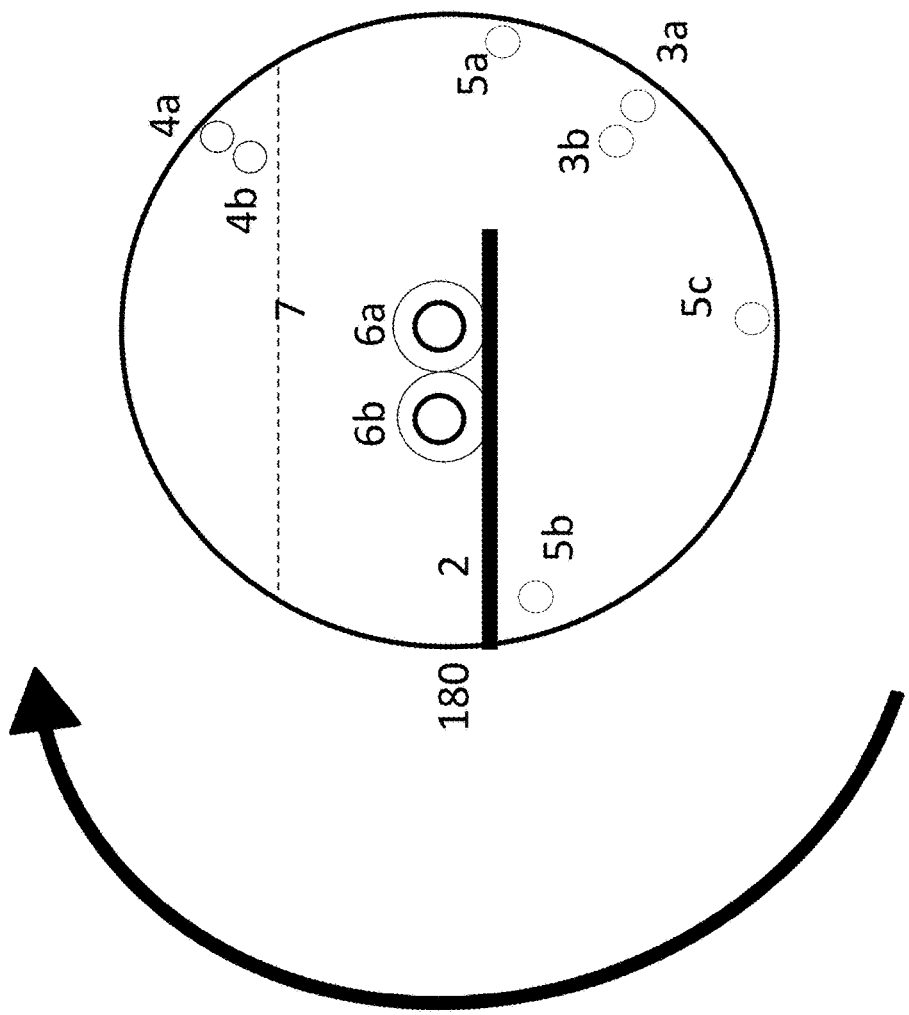
FIG. 4 Position 3 (RA=180)

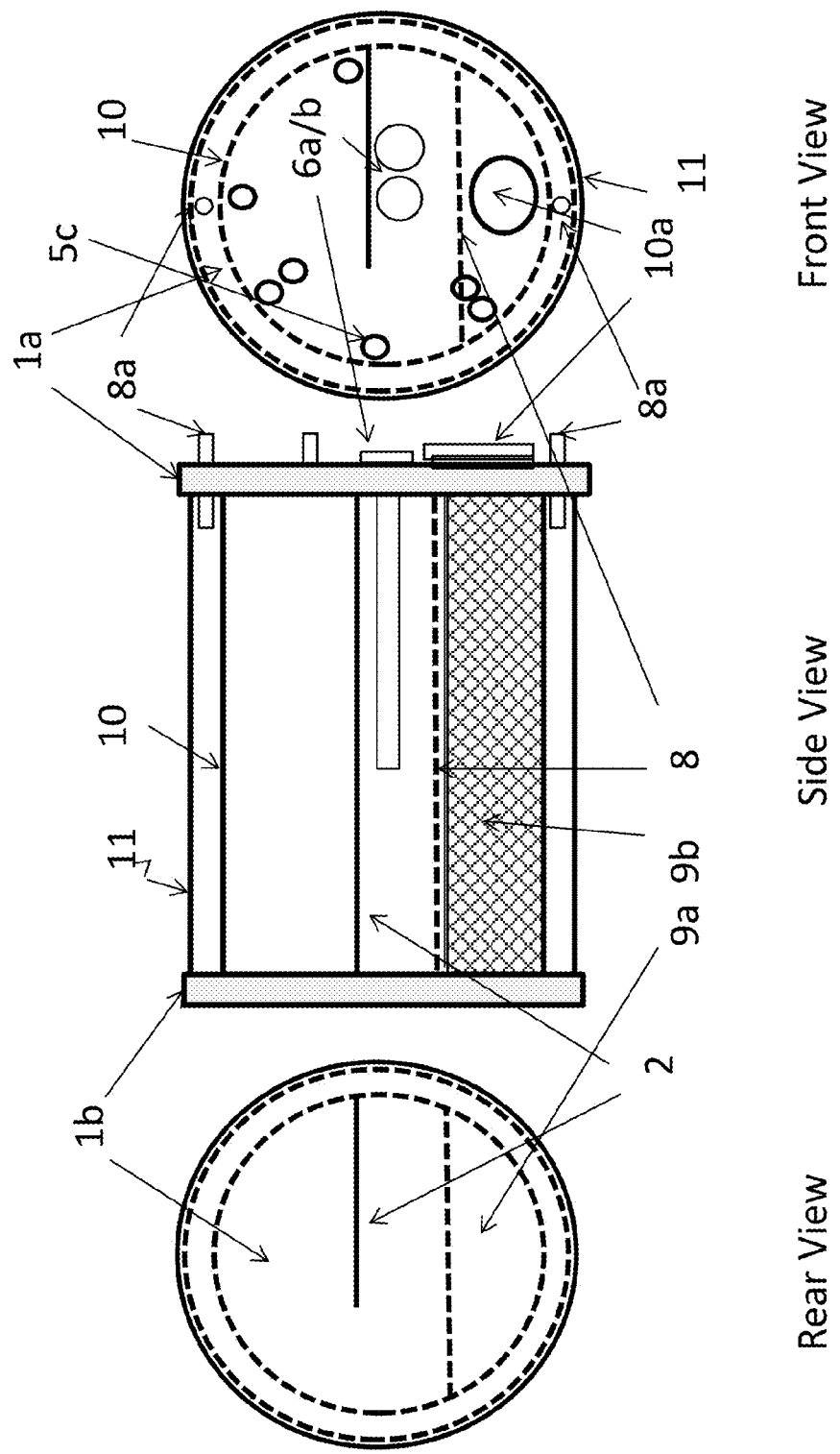

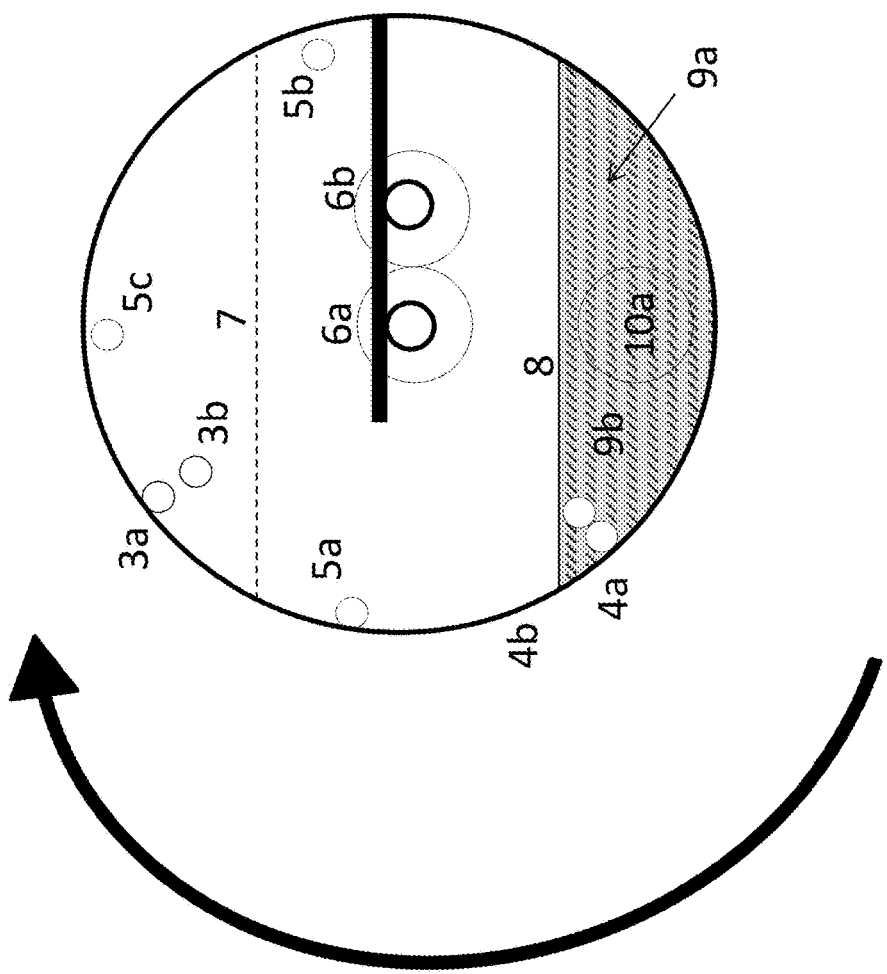
FIG. 6 Position 1 (RA=0)

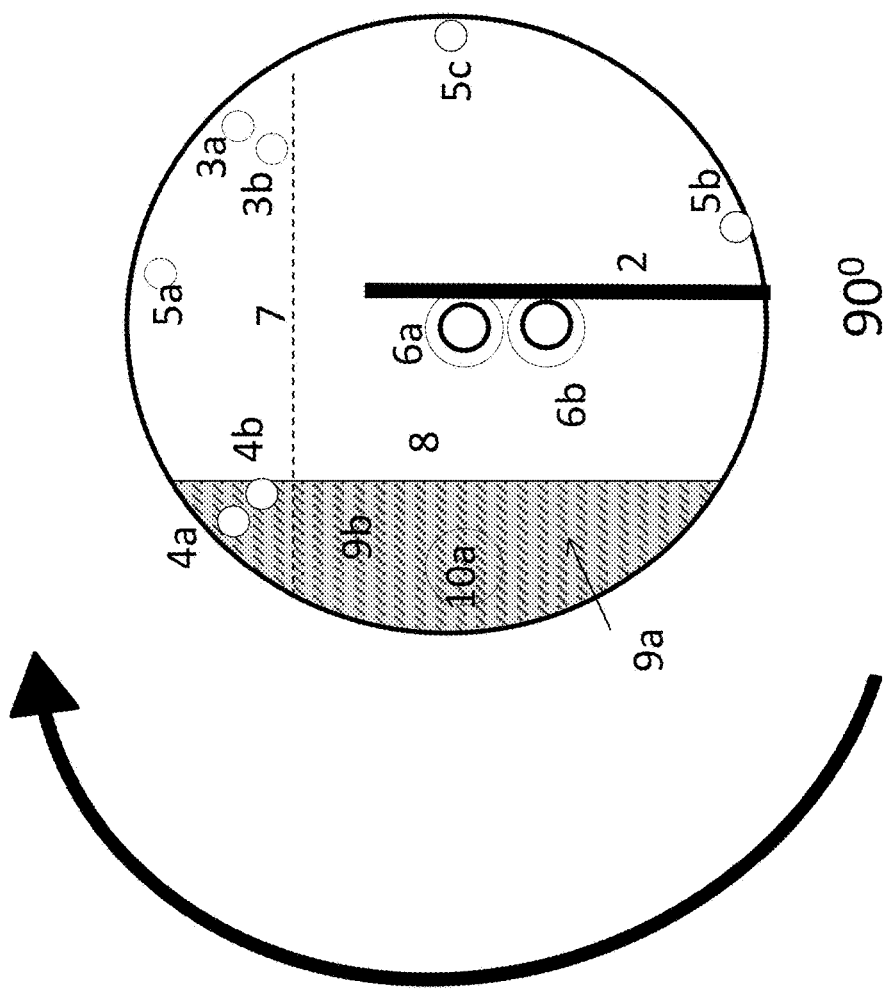

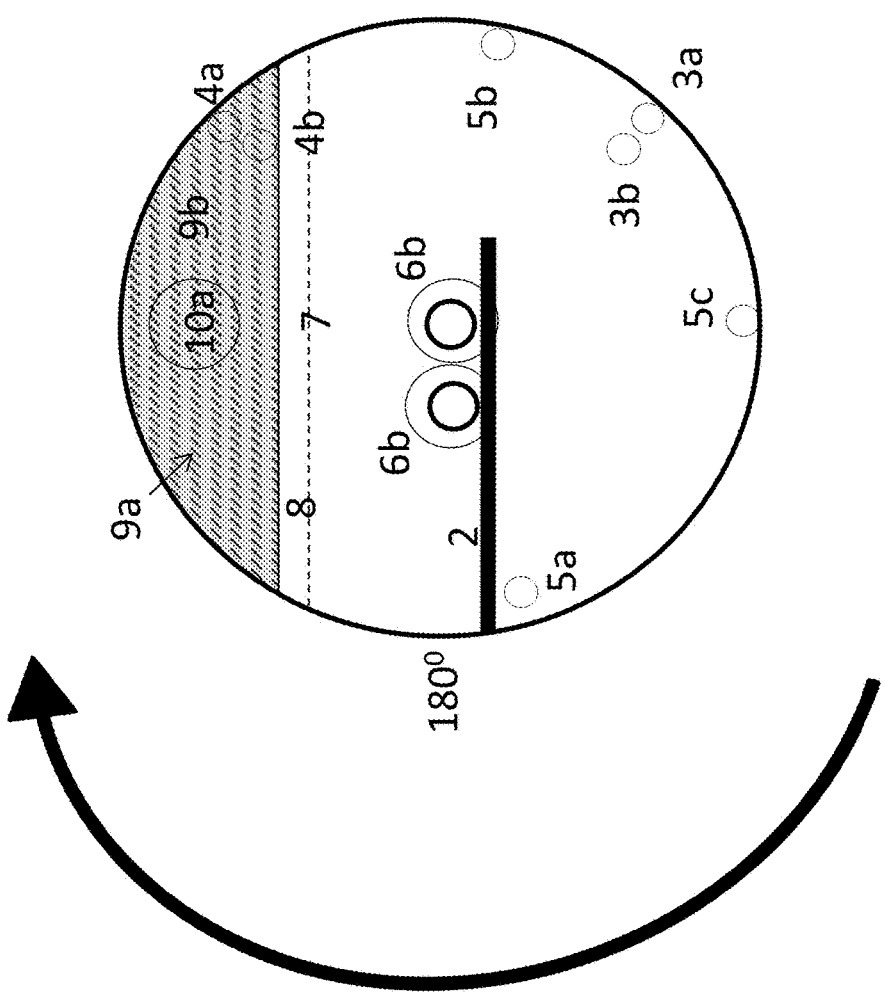

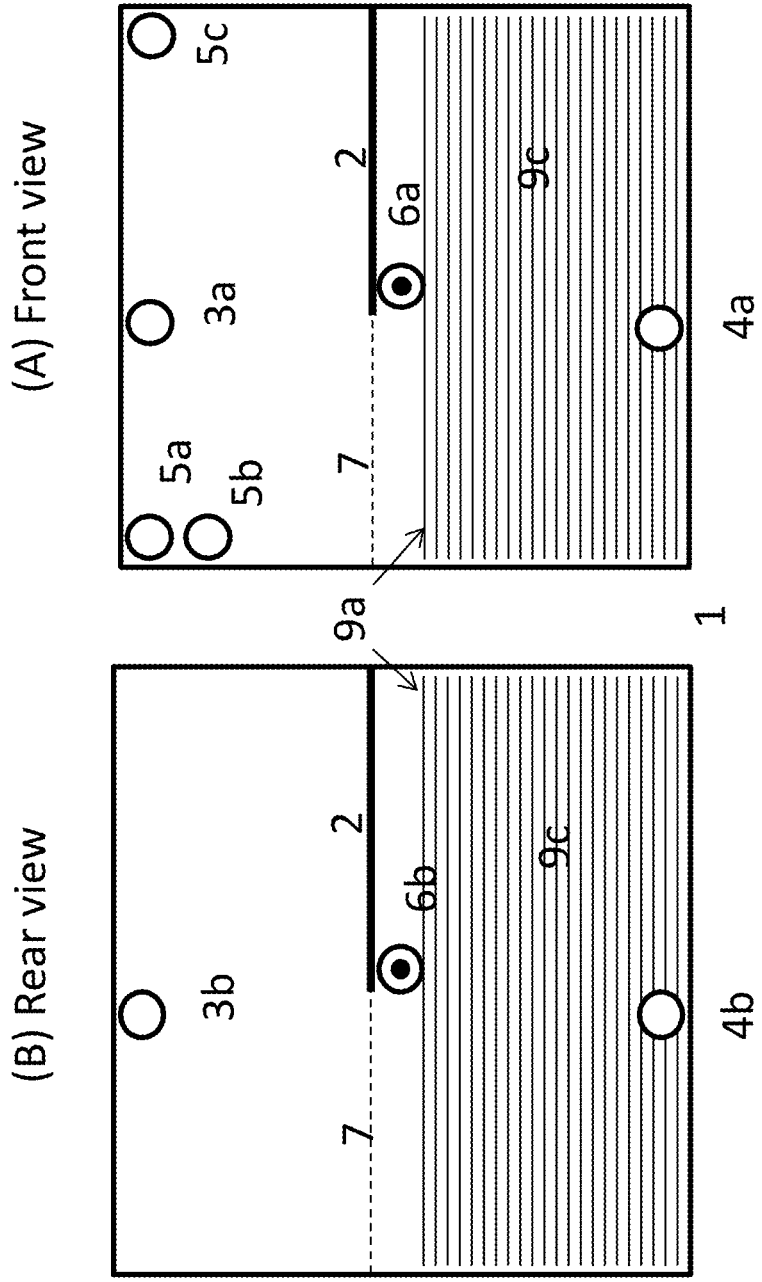
FIG. 9a Position 1 (RA=0) front and rear views

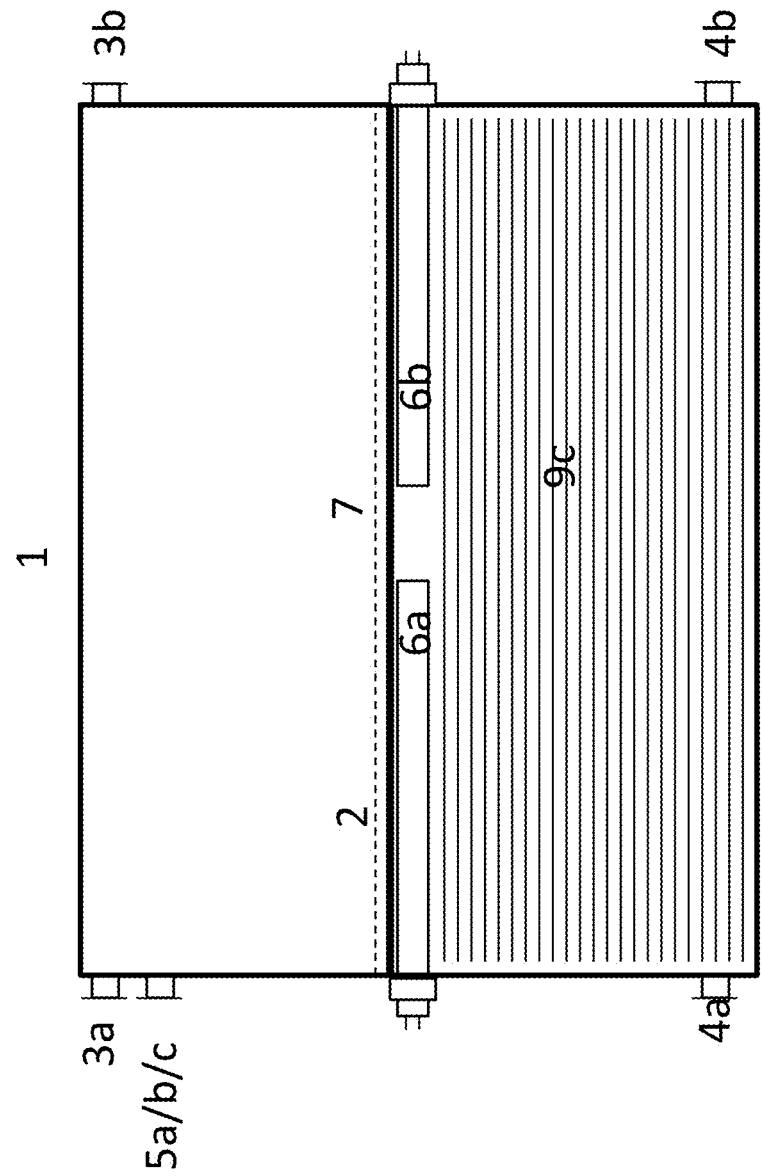
FIG. 9b Position 1 (RA=0) side view

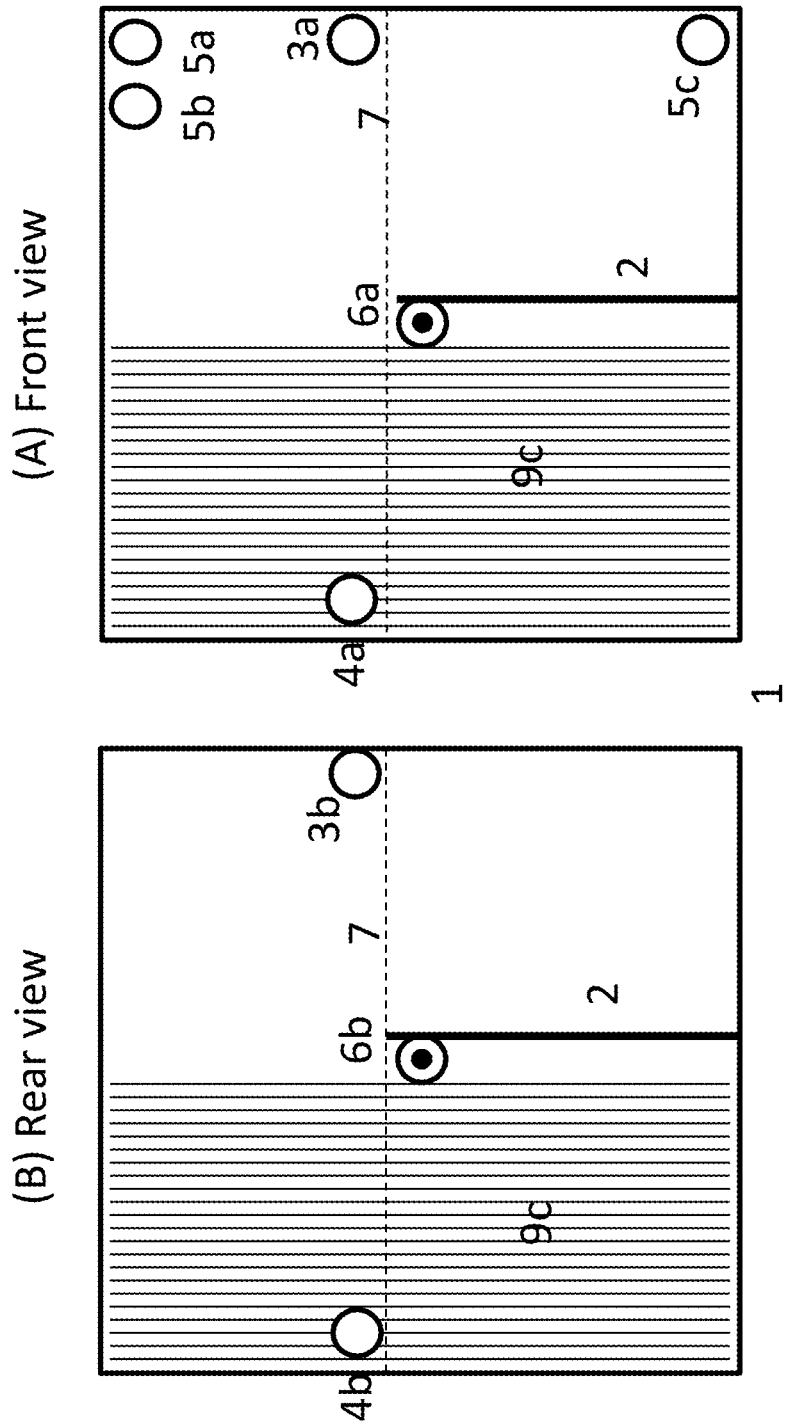
FIG. 10 Position 2 (RA=90)

FIG. 11 Position 3 (RA=180)
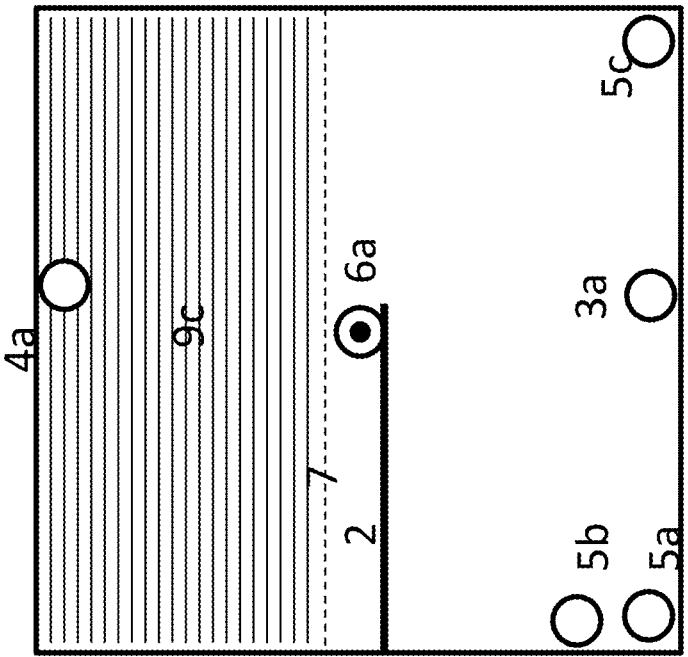
(A) Front view
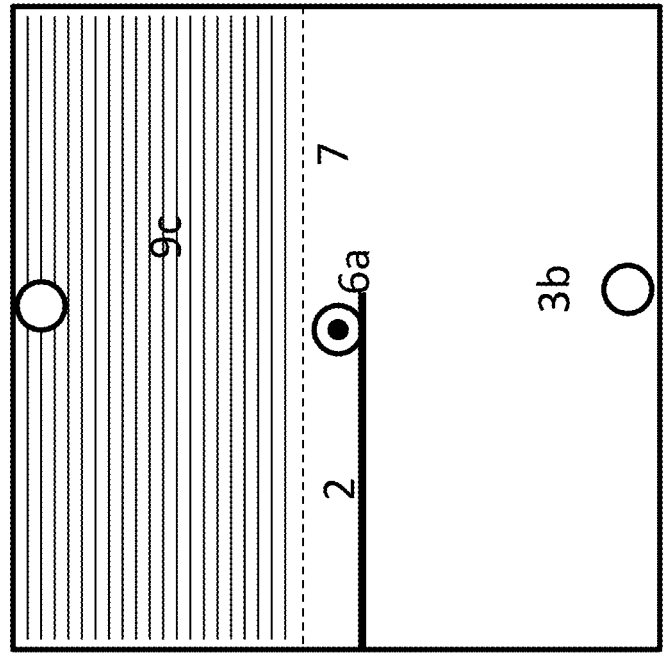
(B) Rear view

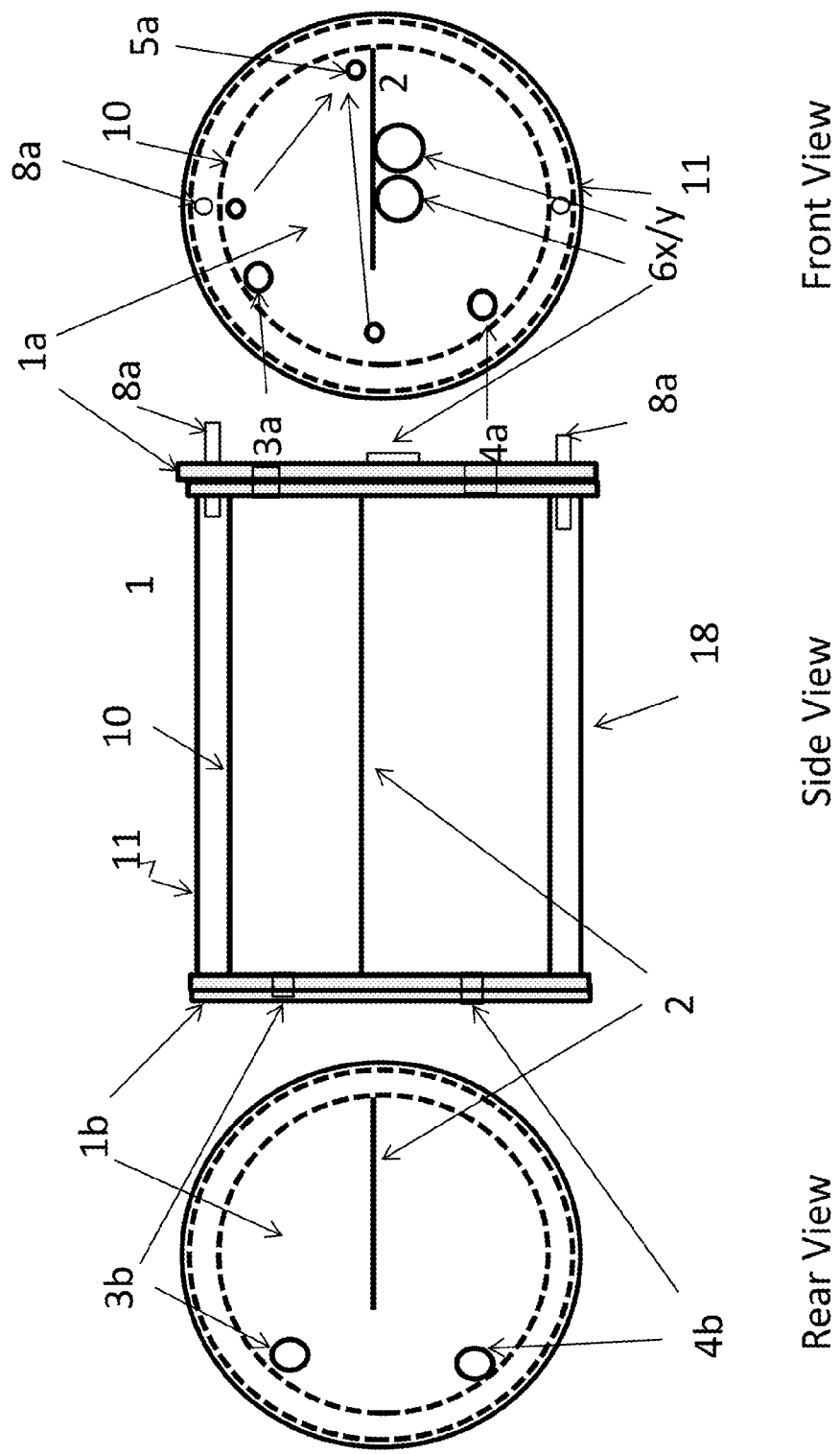

HORIZONTALLY ROCKED BIOREACTOR SYSTEM

This application claims the benefit of U.S. provisional application No. 62/196,833 entitled Horizontally Rocked Packed Bed BioReactor System filed on Jul. 24, 2015; and U.S. provisional application No. 62/267,906 entitled Horizontally Rocked Packed Bed BioReactor System filed on Dec. 16, 2015, both of which are incorporated herein by reference in their entirety.

BACKGROUND

Owing to the lack of cell walls and/or extra cellular materials the culture of eukaryotic cells, animal cells, mammalian cells, and/or tissue is more difficult and more complex because these cells are far more delicate and fragile than microbial cells. The most commonly used device for these cells is the mechanically agitated bioreactor which employs a low shear agitator or applies sparging of air or oxygen to promote the gas-liquid mixing and to provide sufficient oxygen supply to the cells in the culture medium with minimum shear stress. This type of bioreactor, however, is not easy to scale up because the shear distribution is scale-dependent. Adherent cells are always required to attach to some carrier for growth. T-Flasks and roller bottles are the most commonly used devices for these types of cell cultures, but they are extremely labor intensive and lack control capability, and are therefore not economical for large scale production. The microcarrier bioreactor is another common device for these types of cell cultures which substantially increases surface area for cells to attach. The microcarrier bioreactor however requires constant agitation to suspend the microcarrier particles resulting in exposing the sensitive cells to shear stress and low loading capacity of microcarriers. The shear stress environment under agitation is also not favorable for cell attachment and/or virus infection. It is also difficult to separate the attached cells from the medium for frequent medium replacement, making it difficult to operate and incapable of achieving high cell density and is thus less efficient for production.

All of the packed bed bioreactors available on the market utilize macro-porous fiber as a fixed packed bed and use mechanical agitation or a circulation pump to circulate the media through the bed to replenish the nutrients and oxygen. All fixed bed bioreactors that have the bed submerged in the medium rely solely upon the limited pumping force to achieve limited oxygenation for the embedded cells. As a result, these bioreactors have limitations of scalability. Additionally, these fixed bed bioreactors lack the mobility of the bed, limiting the functionality of cell attachment and detachment, cell distribution along the bed, and virus infection.

Another type of bioreactor which is used for solid state fermentation applications is a horizontally rocked fermenter system. The majority of medium components in this bioreactor are solid which is mixed inside the horizontal vessel using its rocking and tumbling motion of the vessel to perform the aerobic or anaerobic fermentation under humidity control. This bioreactor however cannot be used for cell culture wherein the majority is liquid culture material because its rocking motion can only generate little or no mixing effect on liquid culture material even at high rocking rate for sufficient aeration and oxygenation for cell cultures.

Another horizontally rotated bioreactor uses a horizontally rotated vessel using a coaxial membrane tube as an oxygenator for cell cultures. This bioreactor has been used for a wide range of cell culture applications for research and development use. However, due to the limited membrane area and capability of oxygen transfer, this type of bioreactor can only be limited to small scale applications. It has therefore never been applied in large scale application.

SUMMARY

In one aspect, disclosed here is a bioreactor system comprising one vessel assembly comprising at least one closed tubular rigid culture vessel 1; wherein said culture vessel 1 comprises at least one tube 10 and two closed ends 1a/1b made of single use or reusable material; wherein said culture vessel 1 is positioned to lie along the longitudinal axis; wherein said culture vessel 1 is configured to culture cells; wherein said culture vessel 1 comprises at least one baffle 2; wherein the baffle 2 contacts the inside surface and two closed ends 1a/1b of said culture vessel 1, wherein the baffle 2 has a ratio of greater than 0.1 and less than 0.9 of heights of said baffle 2 to the cross-sectional surface of said culture vessel 1 perpendicular to the longitudinal axis; wherein said culture vessel 1 comprises at least one media port 5a/b/c configured to allow culture material to flow in and out of said culture vessel 1; wherein said culture vessel 1 comprises at least one set of two gas ports 3a/b and 4a/b configured to allow the respiratory gas to flow in and out of said culture vessel 1; one reservoir assembly comprising at least one closed container made of single use or reusable material; one rocking apparatus configured to hold and position said culture vessel 1 and rock about the longitudinal axis of the culture vessel 1 along the plane perpendicular to said axis at angle of less than 360 degrees; one pumping apparatus fluidly coupled to at least one media port 5a/b/c of said culture vessel 1 and configured to pump culture material in and out of said culture vessel 1 through said at least one port; one gassing apparatus coupled to at least one set of two gas ports 3a/b and 4a/b of said culture vessel 1 and configured to entering the gas through one gas port and out of said culture vessel 1 through another gas port; one gas blending apparatus coupled to said gassing apparatus and configure to blend the gases including oxygen, nitrogen, carbon dioxide, or air; one monitoring apparatus configured to monitor one or more parameters of said vessel assembly including culture material of said culture vessel 1, reservoir assembly, pumping apparatus, gassing apparatus, gas blending apparatus, and rocking apparatus; and one control apparatus connected wired or wirelessly to vessel assembly, reservoir assembly, pumping apparatus, gassing apparatus, gas blending apparatus, rocking apparatus and monitoring apparatus wherein said control apparatus is configured and programmed to coordinate the positioning and movement of said culture vessel 1 using said rocking apparatus with the culture material pumping in and out of said culture vessel 1 using said pumping apparatus, the passing respiratory gases to enter and exit said culture vessel 1 through one set of inlet/outlet ports and remaining in the gas space at all times using the gassing apparatus; to adjust the gas concentration using said gas blending apparatus and to control the operating parameters of said vessel assembly monitored by said monitoring apparatus.

Also disclosed are systems of any preceding aspect, wherein said baffle 2 is a solid or hollow plate; and wherein the shape of the baffle 2 is flat, curved, angled or helical.

Also disclosed are systems of any preceding aspect, wherein said bioreactor system comprises at least one compartment 9 confined inside of said rigid culture vessel 1 to hold carriers as a fixed packed bed for cells to attach and grow.

Also disclosed are systems of any preceding aspect, wherein the compartment 9 confined inside of said culture vessel 1 to hold carriers as a fixed packed bed for cells to attach and grow is a section of said vessel enclosed by a perforated plate or a screen to loosely hold carriers or to secure multiple layer of non-porous surface plates directly to said vessel.

Also disclosed are systems of any preceding aspect, wherein said compartment 9 of carriers is located in the center of said culture vessel 1 and said set of gas inlet and outlet ports are positioned in the center along the longitudinal axis in both ends of said compartment 9 and said vessel.

In one aspect, disclosed here is a bioreactor system comprising one vessel assembly comprising at least one closed tubular flexible culture vessel 1 and at least one open tubular rigid supporting vessel 18; wherein said supporting vessel 18 comprises at least one tube 10 and two closed ends 1a/1b made of rigid single use or reusable material; wherein said supporting vessel 18 lies along its longitudinal axis and configured to hold and support a flexible culture vessel 1 inside of said supporting vessel 18; wherein said supporting vessel 18 comprising at least one baffle 2; wherein the baffle 2 contacts the inside surface and two closed ends 1a/1b of said supporting vessel 18; and wherein the baffle 2 has a ratio of greater than 0.1 and less than 0.9 of heights of said baffle 2 to the cross-sectional surface perpendicular to the longitudinal axis of said supporting vessel 18; wherein at least one closed tubular culture vessel 1 made of flexible single use material as a bag wherein said bag has the size and shape allowing for close nesting into said one supporting vessel 18 so that said bag closely contacts the entire internal contacting surface of said supporting vessel 18 as the bag is inflated; wherein said culture vessel 1 comprises at least one media port 5a/b/c configured to allow culture material to flow in and out of said culture vessel 1; wherein said culture vessel 1 comprises at least one set of two gas ports 3a/b and 4a/b configured to allow the respiratory gas to flow in and out of said culture vessel 1; one reservoir assembly comprising at least one closed container made of single use or reusable material; one pumping apparatus fluidly coupled to at least one media port 5a/b/c of said culture vessel 1 and configured to pump culture material in and out of said culture vessel 1 through at least one port; one gassing apparatus coupled to at least one set of two gas ports 3a/b and 4a/b of said culture vessel 1 and configured to passing the gas in through one gas port and out of said culture vessel 1 through another gas port; one gas blending apparatus coupled to said gassing apparatus and configure to blend the gases including oxygen, nitrogen, carbon dioxide and air; one rocking apparatus configured to hold and position said supporting vessel 18 and rock about the longitudinal axis along the plane perpendicular to said axis at angle of less than 360 degrees; one monitoring apparatus configured to monitor one or more parameters of said vessel assembly, said reservoir assembly, said pumping apparatus, said gassing apparatus, and said gas blending apparatus and said rocking apparatus; and one control apparatus connected wired or wirelessly to vessel assembly, said reservoir assembly, said pumping apparatus, said gassing apparatus, said gas blending apparatus, said rocking apparatus and said monitoring apparatus wherein said control apparatus is configured and programmed to coordinate the positioning and movement of said vessel assembly using said rocking apparatus with the culture material pumping in and out of said culture vessel 1 using said pumping apparatus, the passing respiratory gases to enter and exit said culture vessel 1 through one set of inlet/outlet ports and remaining in gas space at all times using the gassing apparatus; to adjust the gas concentration using said gas blending apparatus; and to control the operating parameters of said vessel assembly monitored by said monitoring apparatus.

Also disclosed are systems of any preceding aspect, wherein said baffle 2 is a solid or hollow plate and wherein the shape of the baffle 2 is flat, curved, angled and helical.

Also disclosed are systems of any preceding aspect, wherein said bioreactor system comprises at least one compartment 9 confined inside of said flexible culture vessel 1 to hold carriers as a fixed packed bed for cells to attach and grow.

Also disclosed are systems of any preceding aspect, wherein said compartment 9 confined inside of said culture vessel 1 to hold carriers as a fixed packed bed for cells to attach and grow is a section of said vessel enclosed by a perforated plate or a screen to loosely hold carriers or to secure multiple layer of non-porous surface plates directly to said vessel.

Also disclosed are systems of any preceding aspect, wherein said compartment 9 of carriers enclosed by a screen or perforated film is located in the center of said culture vessel 1 and said set of gas inlet and outlet ports are positioned in the center along the longitudinal axis in both ends of said compartment 9 and said culture vessel 1.

BRIEF DESCRIPTION OF THE DRAWINGS

FIG. 1a shows a partial cross sectional view of a double tube-jacketed horizontally rocked culture vessel at 0 degree rocking angle (RA=0) and its front and rear views of two head plates according to the present invention.

FIG. 1b shows a partial cross sectional view of double tube-jacketed horizontally rocked culture vessel at 90 degree rocking angle (RA=90) and its front and rear views of two head plates according to the present invention.

FIG. 2 shows a front view of the single tube horizontally rocked circular cell culture vessel in position of RA=0 where the liquid level is slightly higher than the height of large baffle which is situated directly above the centrally located pH or DO sensor and two sets of two gas inlet and outlet ports according to the present invention.

FIG. 3 shows a front view of the single tube horizontally rocked circular cell culture vessel rotated 90 degrees (RA=90) to the right according to the present invention.

FIG. 4 shows a front view of the single tube horizontally rocked circular cell culture vessel rotated 180 degrees (RA=180) to the right according to the present invention.

FIG. 5 shows a partial cross sectional view of a double tube-jacketed horizontally rocked packed bed culture vessel at 0 degree rocking angle (RA=0) with a packed bed compartment containing carriers and its front and rear views of two head plates according to the present invention.

In the following FIG. 6 through FIG. 8 are illustrated the rocking sequence of a single tube circular cylindrical bioreactor along the longitudinal axis comprising a large baffle and multiple gas inlet and outlet ports and a packed bed compartment containing 3D porous carriers.

FIG. 6 shows a front view of the single tube horizontally rocked circular cell culture vessel in position of RA=0 where the lower one fourth section of the vessel is full of 3D porous carriers and the liquid level is slightly below a level at one fourth of the vessel from the bottom; and a large baffle is situated directly above the centrally located pH or DO sensor according to the present invention.

FIG. 7 shows a front view of the vessel as shown in FIG. 6 but rotated 90 degrees (RA=90) to the right according to the present invention.

FIG. 8 shows a front view of the vessel as shown in FIG. 6 but rotated 180 degrees (RA=180) to the right according to the present invention.

In the following FIG. 9a through FIG. 11 are illustrated the rocking sequence of a horizontally extended single wall rectangular bioreactor containing 2D flat culture surface plates as carriers along the longitudinal axis.

FIG. 9a shows a front view (A) and rear view (B) of the single wall horizontally rocked rectangular cell culture vessel where the lower half of the vessel is full of narrow flat culture surface plates and all submerged under the liquid level and a large baffle is situated right above the sensors according to the present invention.

FIG. 9b shows a side view of the single wall horizontally rocked rectangular cell culture vessel where the lower half of the vessel is full of narrow flat culture surface plates and two sensors are situated in the center of the vessel and a large baffle is situated right above the sensors according to the present invention.

FIG. 10 shows a front view (A) and rear view (B) of the single wall horizontally rocked rectangular cell culture vessel rotated to 90 degrees where one of the gas inlet ports emerges above the liquid surface according to the present invention.

FIG. 11 shows a front view (A) and rear view (B) of the single wall horizontally rocked rectangular cell culture vessel rotated to about 180 degrees where all narrow flat culture surface plates emerge above the liquid surface for oxygenation according to the present invention.

FIG. 12 shows a partial cross sectional view of an open double tube-jacketed horizontally rocked supporting vessel at 0 degree rocking angle (RA=0) and views of its front and rear head plates according to the present invention.

DESCRIPTION OF THE EMBODIMENT

Figure 13:
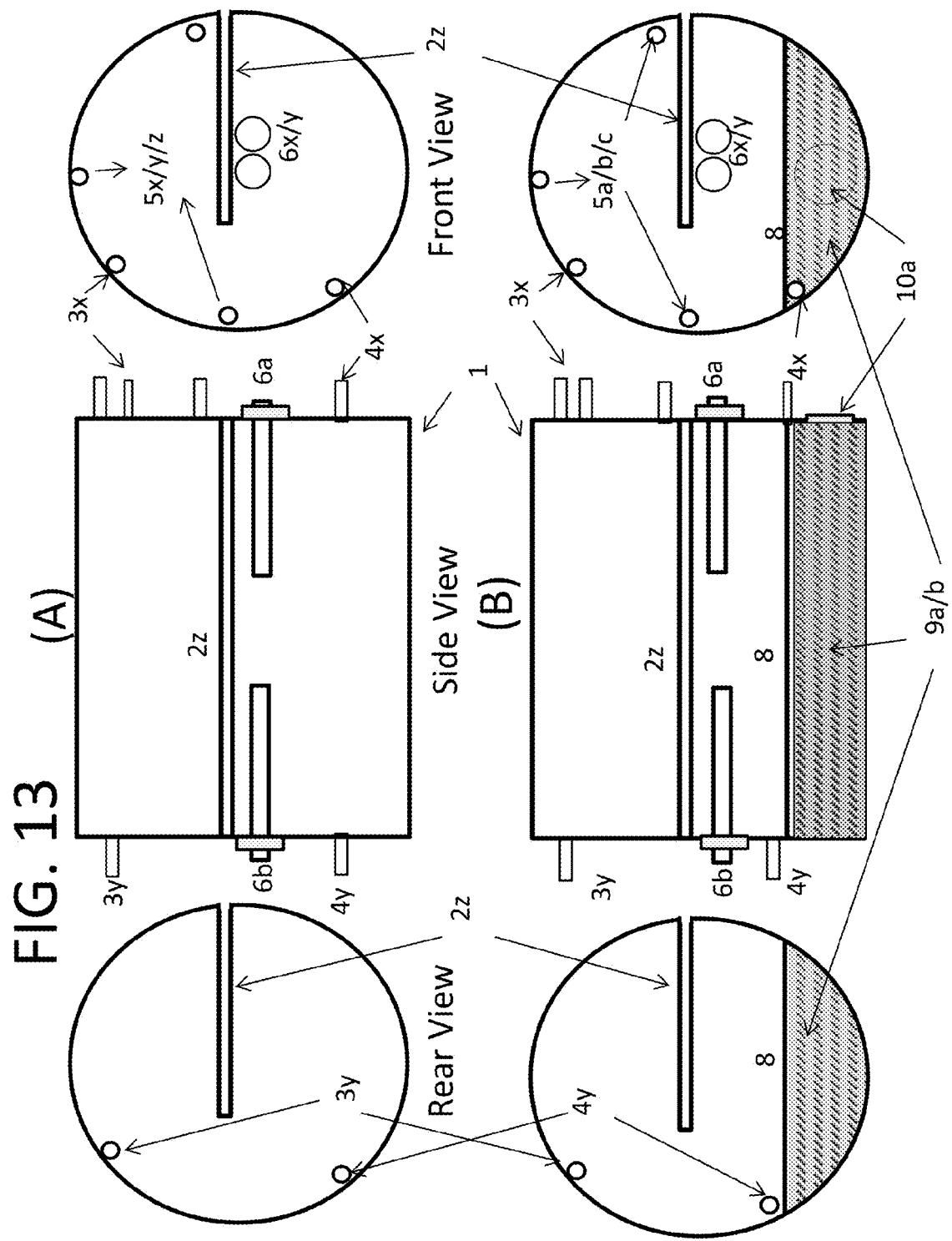
FIG. 13 shows (A) a partial cross sectional view of a closed disposable culture bag and its front and rear views according to the present invention and (B) a partial cross sectional view of a closed packed bed disposable culture bag and its front and rear views according to the present invention.

In the following detailed description, reference is made to the accompanying drawings that form a part here of, and in which are shown by way of illustration several specific embodiments of apparatus, systems, and methods. It is to be understood that other embodiments are contemplated and may be made without departing from the scope or spirit of the present disclosure. The following detailed description, therefore, is not to be taken in a limiting sense The embodiment as described here is a bioreactor system comprising:

a) one vessel assembly comprising at least one closed tubular rigid culture vessel; wherein said culture vessel comprises at least one tube and two closed ends made of single use or reusable material; wherein said culture vessel is positioned to lie along the longitudinal axis; wherein said culture vessel is configured to culture cells; wherein said culture vessel comprises of at least one baffle; wherein the baffle contacts the inside surface and two closed ends of said culture vessel, wherein the baffle has a ratio of greater than 0.1 and less than 0.9 of heights of said baffle to the cross-sectional surface of said culture vessel perpendicular to the longitudinal axis; wherein said culture vessel comprises at least one media port configured to allow culture material to flow in and out of said culture vessel; and wherein said culture vessel comprises at least one set of two gas ports configured to allow the respiratory gas to flow in and out of said culture vessel;

b) one reservoir assembly comprising at least one closed container made of single use or reusable material;

c) one rocking apparatus configured to hold and position said culture vessel and rock about the longitudinal axis of the culture vessel along the plane perpendicular to said axis at angle of less than 360 degrees;

d) one pumping apparatus fluidly coupled to at least one media port of said culture vessel and configured to pump culture material in and out of said culture vessel through said at least one port;

e) one gassing apparatus coupled to at least one set of two gas ports of said culture vessel and configured to entering the gas through one gas port and out of said culture vessel through another gas port;

f) one gas blending apparatus coupled to said gassing apparatus and configure to blend the gases including oxygen, nitrogen, carbon dioxide, or air;

g) one monitoring apparatus configured to monitor one or more parameters of said vessel assembly including culture material of said culture vessel, reservoir assembly, pumping apparatus, gassing apparatus, gas blending apparatus, and rocking apparatus;

h) one control apparatus connected wired or wirelessly to vessel assembly, reservoir assembly, pumping apparatus, gassing apparatus, gas blending apparatus, rocking apparatus and monitoring apparatus wherein said control apparatus is configured and programmed to coordinate the positioning and movement of said culture vessel using said rocking apparatus with the culture material pumping in and out of said culture vessel using said pumping apparatus, the passing respiratory gases to enter and exit said culture vessel through one set of inlet/outlet ports and remaining in the gas space at all times using the gassing apparatus; to adjust the gas concentration using said gas blending apparatus and to control the operating parameters of said vessel assembly monitored by said monitoring apparatus; and/or i) at least one compartment confined inside of said rigid culture vessel to hold carriers as a fixed packed bed for adherent cell cultures.

Disclosed herein are bioreactor systems comprising a vessel assembly, a reservoir assembly a pumping apparatus, a gassing apparatus, a gas blending apparatus, a rocking apparatus, a monitoring apparatus, and a control apparatus.

As disclosed herein said bioreactor system comprises one vessel assembly. Said vessel assembly comprises at least one rigid culture vessels. Said culture vessel comprises at least one tube and two closed ends referred to as head plates bolted together with a gasket between the tube and head plates to form an air-tight vessel. Said vessel is made of reusable material including stainless steel or glass or the like which can withstand steam sterilization conditions; or made of single use rigid material including polymeric material or the like which can be sterilized by gamma irradiation or ethylene oxide or the like. Said polymeric material includes polystyrene, polymethylmethacrylate, polyvinyl chloride, polycarbonate, polysulfone, polyesters, polyamides, polyethylene, polypropylene, or the like. Said tube of vessel is most commonly in circular, oval and square shapes but also in any other polygonal shapes with many sides including but not limited to 3, 4, 5, and 6.

As disclosed herein said culture vessel is a closed system wherein all openings of said culture vessel are connected with only tubing between the inside and outside of said vessel to perform the exchange of culture material including medium and cells through non-invasive valves or pumps during the entire operation so that there is no culture material ever inside of said culture vessel open directly to the external environment through human intervention. Said vessel with two tubes along the longitudinal axis uses the space between two tubes as a jacket to fill with circulating heating or cooling media for temperature control of culture material inside of said culture vessel. Said vessel with one tube along the longitudinal axis uses a heating pad to wrap around said tube or some heating element inserted into a well of said vessel or adopts heating/cooling media to circulate through an internal coil or hollow section of said baffle inside of said vessel for temperature control of culture material inside of said culture vessel.

As disclosed herein, said at least one culture vessel lies along the longitudinal axis and configured to culture cells. Most traditional bioreactor systems are in vertical configuration and require one or more impellers to agitate and mix the culture material inside of the culture vessel. Said bioreactor system lies and rocks the entire vessel along the longitudinal axis at very slow rate of less than 5 rpm without using an agitator to achieve good mixing with minimum shear stress. Furthermore, said horizontally rock culture vessel requires no mechanical seal and motor and makes the construction of said vessel simpler and more economical.

As disclosed herein, said at least one culture vessel comprises at least one baffle wherein said baffle can be in various shapes and configurations including flat, curved, angled and helical or the like and attached or positioned tightly close to all contact internal walls of tube and head plates along the longitudinal axis of said vessel to assure well mixing of culture material inside of said bioreactor even at a slow rocking rate. As used herein, "contacts" refers to any means by which one component is caused to touch or be held in close proximity to, but not necessarily directly touching or touching along the entire adjacent surface of another component (e.g., the baffle and the interior surface of the culture vessel). It is understood and herein contemplated that the when an component such as, for example, a baffle, is in contact with another component such as, for example, the inside wall or ends of a culture vessel, the contact can refer to physical touching or merely close proximity such that the desired function can still be maintained. It is further understood that the contact can comprise sealingly engaging one component to the other (e.g., the baffle to the inside of the culture vessel) or attachment at one or more desired locations. The contact can be achieved through the use of an epoxy, glue, tape adhesive, friction, mechanical pressure, tracks, surface tension, screws, rivets, nails, stables, or the like or any combination thereof. It is understood and herein contemplated that for the function of a component (e.g., a baffle) that is contact to another component to occur, there may be instances where direct physical contact is intermittent or incomplete, such as when physical contact is maintained through mechanical attachment in a few areas allowing for space to occur between the components between points of mechanical attachment. In such instances, contact is deemed to have been maintained so long as the functional properties are maintained. Thus, where the first component (such as, for example, a baffle) is held in close proximity to the second component (such as, for example, the interior of the culture vessel) or attached in certain areas but not sealingly engaging along the entirety length of the adjacent surfaces, the contact is still achieved. For temperature control purposes, said baffle is also applied for heating or cooling use. When said baffle is hollow, a heating or cooling element can be inserted inside or the use of heating or cooling water to circulate inside. At a rocking rate of 2-3, a turn-over of 4-6 times per minute of the total volume of culture material occurs inside of said culture vessel as result of using this baffle. The ratio of heights of said baffle to the cross-sectional surface of said vessel perpendicular to the horizontal axis is greater than 0.1 and less than 0.9. For a circular tubular vessel, for example, the ratio of the heights of said baffle to the cross-sectional surface of said vessel perpendicular to the horizontal axis is the ratio of baffle height to the diameter of circular vessel. Preferably the ratio is 0.45-0.75

As disclosed herein said bioreactor system comprises one reservoir assembly wherein said assembly comprising at least one closed container made of single use or reusable material. Said container are for storage of fresh medium, spent medium, culture material from said culture vessel, inoculum, or the like or for retaining of exhaust gas, etc. Said container is made of single use material including polymeric material or the like as a bag, bottle, tank, etc. or of reusable material including glass, stainless steel etc. Each of said container comprises of at least one vent with air filter and at least one port.

As disclosed herein said bioreactor system comprises a pumping apparatus coupled to at least one medium port configured to allow fluidic culture material to flow in and out of at least one cell culture vessel; said pumping apparatus contains at least one pump to transport the fluid in and out the vessel. Ideally the pump is a peristaltic pump or the like which has no part to contact the fluid and to maintain system integrity. Said fluidic culture material can be inoculum, fresh medium, spent medium, seeded medium, virus solution, enzymatic reagents, etc.

As disclosed herein, said at least one culture vessel comprising at least one set of two gas ports including but not limited to 1, 2 and 3 sets wherein each gas port is connected with a tubing and a pinch valve and configured to couple with a gassing apparatus and a control apparatus to regulate the respiratory gas entering through one gas port and out of said culture vessel through another gas port one set at a time in order to maintain the gas flow is always in the gas space. Said respiratory gas is a gas mixture required for cells to cultivate under various desirable concentration of oxygen, carbon dioxide or the like. Said gassing apparatus is to supply the gas by a gas pump or a pressurized gas cylinder; and for monitoring. Said monitoring apparatus is to monitor the flow rate by a rotameter or mass flow meter and coupled to the control apparatus to control the flow rate by mass flow controller.

As disclosed herein said bioreactor system comprises a gas blending apparatus to alter the gas composition by adjusting the flow rate of each supplied gas using a mass flow controller and controlled by a control apparatus or regulated manually by a rotameter. Said gas blending apparatus is a manifold to combine the supplied gases including air, oxygen, nitrogen and $CO_2$ or the like in a given percent purity to generate a desired concentration of a gas mixture for respiration of said cell culture. Commonly, each of said gas supplies is in a gas cylinder with 100% purity except the air which is supplied by an air pump.

As disclosed herein said bioreactor system comprises one rocking apparatus configured to hold and position said at least one culture vessel; said rocking apparatus is driven by a DC stepping motor that moves in discrete steps. Said motor has multiple coils which are organized in groups named "phases". By energizing each phase in sequence, the motor rotates one step at a time. With computer-controlled stepping, a very precise positioning and/or speed control is achieved. Other options available for positioning control depend on the type of actuator driving the system. An actuator is a mechanical device that moves or controls a specific element or a series of elements within a system. The actuators include stepping motor, pneumatic, brake motor, clutch brake, DC servo system and AC servo system or the like. Said culture vessel is coupled to the shaft of said motor directly or through a driven chain including belt and chain and the like. Said rocker is configured to rock said at least one cell culture vessel about the longitudinal axis along the plane perpendicular to said axis at any angle of less than 360 degrees and at any rocking rate of less than 30 rpm, preferably at angle of less than 180 degrees and rocking rate of less than 5 rpm, and to hold at any angle for any length of time. With this moving flexibility and relative small footprint said system is capable of performing seeding, culturing, medium exchange, cell detachment and harvesting all in one place and in one closed vessel.

As disclosed herein said bioreactor system comprises one monitoring apparatus configured to monitor one or more parameters of culture material in said vessel assembly, reservoir assembly, pumping apparatus, gassing apparatus, gas blending and rocking apparatus. Said parameters of said culture vessel and culture material of said culture vessel include all biophysical, biochemical and biological properties such as temperature, pH, pressure, dissolved oxygen (DO), dissolved carbon dioxide (DCO2), glucose, lactate, glutamine, glutamate, ammonium, pH, sodium, potassium, osmolality, protein, nucleic acid, total cell number, cell viability, cell morphology and the like. Said parameters are monitored using sensors, biosensors, imaging devices, on-line or off-line biochemical or biophysical analyzers or the like. In said vessel assembly and reservoir assembly the pressure for system integrity and filter blockage using the pressure sensor is monitored.

In said pumping apparatus pumping rate is monitored using the rotating speed of shaft of said peristaltic pump. In said gassing apparatus and gas blending apparatus the flow rates of each gas is monitored using mass flow meter. In said rocking apparatus its rocking angle, position and rate using the stepping motor or the like is monitored.

As disclosed herein said bioreactor system comprises a control apparatus wherein said control apparatus may include one or more computing devices capable of processing data; microprocessors, programmable logic arrays, data storage, input devices, output device; human machine interface (HMI) and programmable logic control (PLC) etc. Said control apparatus is configured to connect wired or wirelessly to each element of said bioreactor system including said vessel assembly, said reservoir assembly, said pumping apparatus, said gassing apparatus, gas blending apparatus, rocking apparatus and monitoring apparatus and the like. Said control apparatus is configured and programmed to coordinate the positioning and movement of said culture vessel using said rocking apparatus with the pumping culture material in and out of at least one cell culture vessel using said pumping apparatus, the control of the passing respiratory gas in and out of said culture vessel using said gassing apparatus, to adjust the gas composition and gas flow rate using said gassing and blending apparatus and to control the operating parameters of said vessel assembly including temperature, pH, DO, pressure, glucose or the like is monitored by said monitoring apparatus. Said control apparatus controls the on/off of each pinch valve to regulate the gas flow through each set of gas inlet and outlet ports to permit the gas flow pattern during the rocking motion to always maintain the gas flow above the liquid phase. In such a manner the liquid volume or loading capacity of said vessel can be significantly increased compared to using only one single set by at least 40-50%. It also mitigates the foaming problem because the gas flow always remains only in the gas phase. Said control apparatus described herein provides a fully automated solution to accomplish one or more processes including seeding, culturing, medium exchange, cell detaching and harvesting cells from said culture vessel.

As disclosed herein said culture vessel comprises at least one compartment confined inside of said vessel by a screen or perforated plate to hold carriers as a fixed packed bed for adherent cells to attach and grow. Said carriers are 2D non-porous smooth flat or curved surface or 3D porous carriers or scaffolds. A 2D carrier such as that made of polystyrene or the like material is a non-porous surface for cells to attach and form a monolayer culture. A 3D carrier or scaffold such as that made of glass bead, ceramic, polyester fiber, polyurethane fiber or the like material has a porous surface for cells to attach and form a three dimensional multilayer culture. Both carriers are commonly treated with plasma to change the surface properties to improve adhesion. If these carriers are loosely held individuals, they are packed as a bed by a perforated plate or a screen secured to said culture vessel. The flexibility of rocking motion of said culture vessel with a packed bed of carriers inside of said compartment permits the carriers to alternately expose the cells directly to gas space and submerge the cells to the medium for nutrient replenishment. This disclosure provides the most efficient oxygenation while requiring little to no shear stress to accommodate the extra demand of oxygen for the high cell density culture.

As disclosed herein said vessel assembly comprising said culture vessel without having the compartment is intended to be used for suspension cultures which require no carrier for cells to attach and grow. However, it is also effectively used for adherent cultures with microcarriers. Compared to a microcarrier culture using conventional mechanically agitated bioreactor, this system requires no agitator for mixing the microcarrier beads and thus enabling to reduce the shear stress to the cells and microcarrier beads. It also enables to increase the maximum microcarrier loading concentration to increase the cell density with no concern of sedimentation of said beads under limited agitation and shear force. It also allows using significantly less volume of medium initially for seeding and thus enabling to increase the efficiency of cell attachment to the beads.

In FIG. 1a is illustrated a double tube horizontally rocked cell culture vessel comprising two tubes 10, 11 and head plates 1a, 1b at two ends bolted together with a gasket between the tubes and head plates to form an air-tight culture vessel at position designated as 0 degree of rocking angle (RA=0). The front view shows the head plates 1a and 1b; a large baffle 2 welded to at least one inner wall of tube 10 of vessel or head plates 1a and 1b and tightly close to the other not welded walls to minimize the liquid leaking through the contact edges of the baffle with gasket allowing the majority of the medium to flow over the opening top space of said baffle 2 during the rocking motion; ports 3a/3b, and 4a/4b for two sets of gas inlet and outlet ports; ports 5a/b/c for feeding of medium reagents or the like; ports 6a/b for sensors. The side view shows the front head plate 1a and rear head plate 1b of the double tube vessel 1 with the large baffle 2. The space between the two tubes 10 and 11 serves as a jacket for heating or cooling water pumped through ports 8a, and circulates between said space to control the temperature of the vessel. The rear view shows the rear head plate 1b with baffle 2.

In FIG. 1b is illustrated the same vessel of FIG. 1a but rotated 90 degrees to the right from the previously designated 0 degrees position to further reveal the position and configuration of the baffle 2. In the side view, the baffle 2 is shown to closely attach to all three contacting walls 12, 13 and 14 by welding or tightly attached with gasket in between the baffle and said walls. The tubular vessel is filled with culture material to reach liquid level 7 which is greater than 50%, preferably 75%, of the total vessel volume. In the following FIG. 2 to FIG. 4 is illustrated the rocking sequence of the bioreactor system. The rocking sequence of the culture vessel varies the position from the designated rocking angle RA=0 degree to RA=180 degree and back to RA=0. During the rocking sequence FIG. 2 to FIG. 4 illustrate how the gas flow is controlled and alternated between two sets of gas inlet and outlet ports in order to keep the gas flow above the liquid level at all times so that the working volume of liquid medium inside the vessel is maximized (>75%) and no foaming problem is created. Because the large baffle 2 is in vicinity to the center of and attached or tightly close to all three contact walls (i.e. the inner vessel wall 10 and front 1a and rear head 1b plates), the entire culture medium is completely turned over 2 times per every rock per minute during the 180 degree rocking motion. With this specially designed large baffle 2 in the vessel the rocker is capable of driving the vessel to three positions (0°, 90° and 180°) and holding at each position for any length of time to execute various specified actions for the best efficiency of mixing, oxygenation and seeding, infection, transfection, culturing, medium exchange, and harvesting. With an addition of a compartment 9a in the vessel 1 to hold the carriers 9b as a packed bed for adherent cells to attach the rocking motion of said vessel 1 permits the packed bed of carriers 9b to alternately expose the cells directly to gas space and submerge the cells to the medium for nutrient replenishment. This disclosure provides the most efficient oxygenation while requiring little to no shear stress to accommodate the extra demand of oxygen for the high cell density culture. This is made possible from the direct contact of oxygen to the cells with no requirement of the typical high shear force to facilitate the oxygen transfer through the bulk liquid phase.

In FIG. 2 is illustrated the front view of a single tube horizontally rocked circular culture vessel in position 1 (referred to as rocking angle RA=0). The front view shows that the front plate 1a has two sets of gas inlet and outlet ports 3a/3b and 4a/4b, two feeding ports 5a (for fresh medium or the like) and 5b (for sodium carbonate or other reagent), and port 5c for emptying or harvesting and sensor ports 6a, and 6b for sensors. The medium is filled through port 5a from the medium reservoir in the reservoir assembly to the liquid level 7 which is higher than the height of the baffle 2 and about 75% of the full vessel volume. The large baffle 2 is closely attached to the vessel and situated directly above the centrally located pH and DO sensors 6a, 6b which are always submerged in the liquid during the rocking sequence. On each 180 degree turn, the baffle 2 moves the entirety of liquid around the vessel once. In this position of RA=0 the gas inlet port 3a and outlet port 3b are opened and 4a/4b is closed. Using the gassing apparatus the respiratory gas mixture enters into the vessel through 3a and exits through port 3b.

In FIG. 3 is illustrated the front view of the vessel being rotated 90 degrees to the right from the designated position of RA=0. While moving from position 0° to 90° the baffle 2 forces the liquid downward and flows over the baffle 2. This flow movement creates a waterfall-like action and results in good mixing and oxygenation of liquid inside the vessel 1 even at very slow rocking rates. In this position 2 (RA=90) both gas inlet and outlet ports 3a/b and 4a/b are exposed to the gas space. Both 3a and 3b remain open. Since Port 3b is situated directly above the initial liquid level, any excess liquid above the designated level will be pushed through Port 3b into the overflow container in the reservoir assembly. This would be for the case of running perfusion mode in which a constant liquid volume is remained in the vessel. After a given holding time at this position Ports 3a/3b are closed and 4a/4b are opened and the vessel continues to move toward the next position 3 (RA=180).

In FIG. 4 is illustrated the front of the vessel being further rotated 90 degrees to the right during the rocking sequence using the rocking apparatus. In this position 3 (RA=180) if it is time for harvesting, port 4b is closed and port 5c is opened. The existing medium in the vessel is emptied through port 5c by gravity and from the positive pressure resulted from the closing of outlet port 4b. If it is not time for harvesting, the sequence is reversed and rocking direction is also reversed. All of these sequences are coordinated by the control apparatus.

As disclosed herein said bioreactor has an addition of at least one compartment confined inside of said vessel to hold carriers other than microcarriers as a fixed packed bed for adherent cells to attach and grow. Said carriers are 2D non-porous flat or curved culture surface or 3D porous surface carriers or scaffolds. A 2D carrier such as that made of polystyrene or the like materials is a non-porous flat or curved smooth surface for cells to attach and form monolayer culture. A 3D porous carrier or scaffold such as that made of glass bead, ceramic, or fibers made of polyethylene terephthalate, polyester, or polyurethane or the like materials has a porous surface for cells to attach and form three dimensional multilayer cultures. Both carriers are commonly treated with plasma to change the surface properties to improve adhesion. If these carriers are loosely-held individuals, they are packed as a bed by a perforated plate or a screen. If these carriers are rigid plates, they are directly secured to said vessel to form a multi-layer vessel or enclosed by a perforated plate or a screen as a compartment confined inside of said vessel.

Referring to FIG. 5, a double tube-jacketed horizontally rocked cell culture vessel identical to FIG. 1a and FIG. 1b adds a compartment 9a enclosed by a perforated screen 8 to hold the carriers 9b for cells to attach. The cap 10a is assessable for filling, removing, or sampling of carriers 9b. The vessel is constructed by glass and/or stainless steel for autoclave or steam sterilization in place. In the following FIG. 6 to FIG. 8 is illustrated the rocking sequence of the bioreactor system comprising of a compartment to hold a packed bed of carriers for adherent cells to attach. The sequence and course of action at each position are identical to those shown in FIG. 2 to FIG. 4 except that the cells are to be immobilized in the carriers and thus the process involves additional steps of cell attachment, detachment, infection, transfection, medium exchange etc. As previously shown the rocker drives the vessel to three positions (0°, 90° and 180°) and holds at each position for any length of time to execute various specified actions for the best efficiency of mixing, oxygenation and seeding, infection, transfection, cell attaching, detaching, culturing, medium exchange, harvesting. Best of all, the rocking sequence allows this moving packed bed bioreactor to alternately expose the cells directly to the gas phase and submerge to the medium phase for the best oxygenation with little to no shear stress.

In FIG. 6 is illustrated the front view of a single tube horizontally rocked circular cell culture vessel of which the compartment 9a is about one-fourth filled with 3D porous carriers in position 1 (designated as RA=0). The vessel is identical to the one shown in FIG. 2 except a compartment 9a is enclosed with a perforated screen 8 for holding the carriers 9b and a cap 10a accessible for sampling or filling of the carriers. Since the cells are required to attach to the carriers, this system allows the initial inoculum to be seeded with minimum volume (same volume of compartment) or the most concentrated seed for best efficiency of attachment. The seed is initially filled to the level slightly above the screen 8 to just cover the compartment 9a. Subsequently, the vessel is rocked briefly in full 180 degrees or small angle of 5-10 degrees to assure the uniformity and oxygenation for the best cell attachment. The gas ports 3a and 3b are open and remain open during the brief rocking process of smaller angle or closed and switched to ports 4a/4b if full rotation of 180 degrees is taken. The similar procedure or sequence is applied for virus infection, DNA transfection and enzymatic detachment where the reagent can be most concentrated for best efficiency of each action. The seeding stage is completed when the seeding cells are sufficiently attached to the carrier, e.g. >90%; the medium is filled to level 7 through port 5a and the culturing stage begins. In this position the gas inlet port 3a and outlet port 3b are opened and 4a/4b is closed. The respiratory gas mixture enters into the vessel through 3a and exits from port 3b using the gassing apparatus.

In FIG. 7 is illustrated the front view of a single tube horizontally rocked circular cell culture vessel of which the compartment 9a is about one-fourth filled with 3D porous carriers in position 2 (RA=90). While moving from position 0° to 90° the baffle 2 forces the liquid down and flows over the baffle like an overflowing river over a dam. This movement along with the waterfall effect creates good mixing and oxygenation of liquid inside the vessel even at very slow rocking rates. In this position 2 (RA=90) both gas inlet and outlet ports; 3a/3b and 4a/4b are exposed to the gas space. Both 3a and 3b remain open. Since Port 3b is situated directly above the initial liquid level, any excess liquid above the designated level will be pushed out through Port 3b into the overflow container in the reservoir assembly. This is for the case of running a perfusion mode to maintain a constant liquid volume inside of the vessel. After a given holding time at this position Ports 3a/3b are closed and 4a/4b are opened and moves onto the next position 3.

In FIG. 8 is illustrated the front view of a single tube horizontally rocked circular culture vessel of which the compartment 9a is about one-fourth filled with 3D porous carriers in position 3 (RA=180). When the vessel moves from position 90° to 180° the carrier section is completely exposed to the gas space for the best efficiency of oxygenation. If it is time for medium exchange, port 4b is closed and port 5c is opened. The existing medium in the vessel is pushed out by the positive pressure and emptied through port 5c to the container in the reservoir assembly. This is followed by closing port 5c, opening 4b and port 5a and then activating a feeding pump. A given amount of the fresh medium from the medium storage container in the reservoir assembly is then pumped in through medium port 5a and then port 5a closes after refilling is complete. After a given holding time to complete the action in this position, the rocker is ready to proceed by reversing the rocking direction from 180° to 0°.

In the following FIG. 9a to FIG. 11 are illustrated the rocking sequence of a rigid rectangular vessel to perform the dynamic culture as roller bottle culture method wherein said vessel 1 comprises of multiple parallel culture surface plates 9c filled in half of said vessel and a large baffle 2 is attached to all three of the contact walls. Ports 3a/3b, and 4a/4b are two sets of the gas inlet/outlet ports. Ports 5a and 5b are the feed inlet and 5c the outlet ports. The gas inlets and outlets 3a/b, 4a/b are controlled to permit the gas mixture to remain the gas flow in the gas space at all times. The cells attach and grow on the 2D non-porous culture plates 9c as most of the traditional static cultures. Most of traditional culture methods are static culture using petri-dish, T-flask or multi-layer flask or vessel wherein the cells attach and grow on the bottom surface of each culture vessel with the nutrient from medium above the surface and oxygen supply through the diffusion from the gas space above. For dynamic culture both cells and medium move relatively against each other constantly or frequently like a roller bottle culture method wherein the cells attach to the inner surface of bottle and move against the medium and air alternately as the bottle is rolling. Under this dynamic culture method the mass transfer of oxygen and nutrients are active and more effective. Therefore, the gap between two layers of this multiple layers of flat surface plates 9c in this vessel can have tight gaps of about 1.5-3 mm between two plates to maximize the contact surface area which is in contrast to the normal gap of 15 mm in traditional multi-tray vessels such as Cell Factory or Cellstack. This culture vessel is made of single use polymeric material such as polystyrene or the like. Due to its high oxygen transfer efficiency by direct exposure to the gas phase as roller bottle method this system requires only extremely slow rocking rate which yields little to nearly no shear stress.

The carrier compartment 9a is initially located in the bottom of the vessel and designated as position 1 (RA=0) as shown in FIG. 9a. As shown above in other cases, the rocker drives the vessel to three positions (0°, 90° and 180°) as shown in FIG. 9a to FIG. 11 and holds at each position for any length of time using the rocking apparatus to execute various specified actions for the best efficiency of mixing, oxygenation, seeding, infection, transfection, cell attaching, detaching, culturing, medium exchange, and harvesting. Best of all, the rocking sequence allows to alternately expose the cells directly to the gas phase and submerge to medium phase for the best oxygenation with little to no shear stress. As the vessel 1 rotates, the large baffle 2 pushes the culture material over the baffle 2 like an overflowing river over a dam and turns the culture material over to create good mixing even at slow rocking rate.

In FIG. 9a are illustrated the front and rear views of a single tube horizontally rocked rectangular culture vessel half-filled with multiple narrow 2D flat culture surface plates 9c in position 1 (RA=0 degrees). The front view shows that the front side of said vessel 1 has two gas inlet ports 3a and 4a, a set of inlet feed ports 5a (medium) and 5b (sodium bicarbonate or other reagent), and sensor port 6a for sensor. The medium is filled to the liquid level 7 by a pump of the pumping apparatus through port 5a. Port 5c is for the medium outlet. In this position the gas inlet/outlet ports 3a/3b are opened and 4a/4b are closed. The respiration gas mixture generated from the gas blending apparatus enters into the vessel through 3a and exits from port 3b in the rear vessel using the gassing apparatus to a gas retaining container in the reservoir assembly. The liquid level 7 is always above the sensor port 6a. A special baffle 2 as previously described above is firmly attached to all three contact walls in the vessel 1 and situated right above the sensor 6a. The rocker of the rocking apparatus is held in this position for a given time to complete the functions such as seeding, filling, nutrient uptake, etc. coordinated by the control apparatus.

In FIG. 9b is illustrated the side view of a single tube horizontally rocked rectangular culture vessel half-filled with 2D flat culture surface plates 9c in position 1. The side view shows two sensors 6a and 6b which are in the center of the vessel 1 and underneath the liquid level 7 and will always remain the same position during the entire 180 degree rocking process.

In FIG. 10 are illustrated the front and rear views of a single tube horizontally rocked rectangular cell culture vessel 1 half-filled with 2D flat culture surface plates 9c in position 2 (RA=90 degree). In this position it shows that the vessel has rotated 90 degrees from RA=0 position 1 and the plates 9c are vertical and perpendicular to the liquid level; and the bottom gas inlet/outlet 4a/4b ports emerge above the liquid level. The ports 3a/3b remain open and 4a/4b remain closed. If the bioreactor system is conducting the perfusion culture, the excess fed medium is pushed out through port 3b and the liquid level remains in the original level 7. After holding at this position for a given time to complete the action, the ports 3a/3b are closed and 4a/4b opened, the rocker in the rocker assembly moves onto the next position 3 (RA=180).

In FIG. 11 are illustrated the front and rear views of a single tube horizontally rocked rectangular cell culture vessel 1 half-filled with 2D flat surface plates 9c in position 3 (RA=180 degree). In this position it shows that the vessel 1 has rotated to 180 degree position and the feed outlet port 5c is in the lowest position and the carrier plates are entirely exposed to the gas space. If the medium exchange is needed, the gas outlet port 4b is closed and feed outlet port 5c is opened; the entire medium is emptied through port 5c or collected in a receiving container in the reservoir assembly in this position. After holding at this position for a given time to complete the action, the rocker in the rocker assembly reverses the direction and rotates in the reverse sequence from RA=180 to RA=0 position.

As disclosed herein said bioreactor system has an addition of at least one compartment confined inside of said vessel 1 to hold carriers 9b or 9c as a fixed packed bed for adherent cells to attach and grow wherein said compartment 9a is the entirety of said vessel 1. Said compartment 9a or the entire vessel 1 is filled with said 2D or 3D carriers. However, only half of said vessel 1 is filled with medium. Under this configuration said rocking apparatus requires rotating 360 degrees instead of 180 degrees as described above and an additional set of 2 gas inlet/outlet ports is required to install at 90 degrees opposite to the other two sets 3a/3b and 4a/4b so that the gas flow always remains above the liquid phase at all time. Said configuration increases the surface area of carriers, but requires more frequent medium replacement to meet the nutrient requirement and also presents more drastic change of internal nutrient concentration.

As disclosed herein said culture vessel wherein said compartment of carriers enclosed by a screen or perforated tube is situated in the center of said culture vessel and said gas inlet and one outlet are situated in the center of horizontal axis in both ends of said compartment and said vessel. For suspension cells the perfusion culture is able to use the packed bed of carriers as a filter to entrap and retain the cells inside of the culture vessel or bag without the requirement of another cell retaining device. Said bioreactor system accomplishes this objective by having the culture material along with the respiratory gas enter into said vessel through the bed of carriers to retain the cells and to allow the medium exiting from the center of said vessel while the constant volume remains inside of said vessel. The volume of medium in said culture vessel is about half of total vessel volume. The inlet gas enters from the center of one end of vessel and exits from another end along with the exiting medium in such that the gas remains above the liquid phase and mitigates the foaming problem. The rocking motion of the carrier compartment also allows the imbedded cells in the carriers to alternately expose and submerge to gas and liquid phases to achieve the best oxygenation.

Figure 14A:
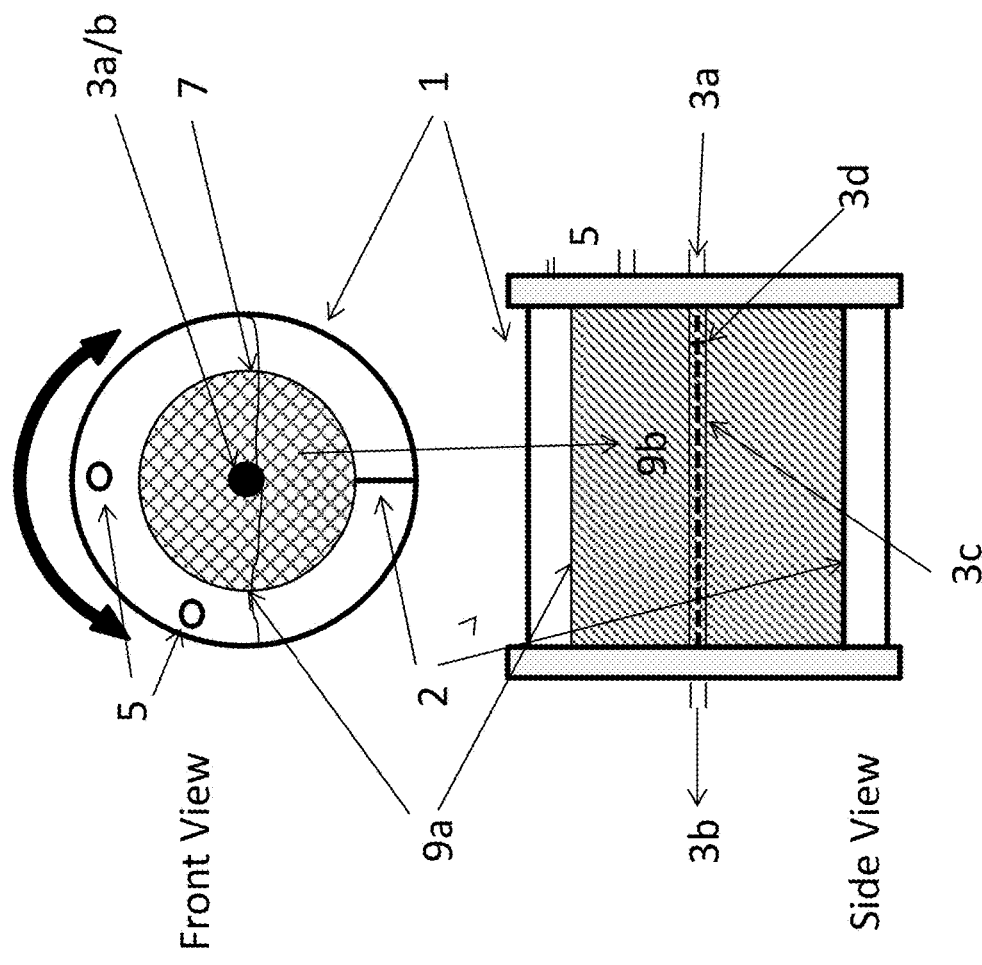
FIG. 14A shows the front and side views of a closed culture vessel wherein its carrier compartment enclosed by a perforated tube is situated in the center of the culture vessel along the horizontal axis according to the present invention.

In FIG. 14A is illustrated the front and side views of said culture vessel 1 wherein said carrier compartment 9a is situated in the center of said culture vessel 1 and a perforated tube 3c situated in the center along the longitudinal axis with only one gas inlet 3a and one outlet 3b in each end of said tube 3c and has a partition 3d in said tube 3c toward the inlet end so that the inlet gas diffuses quickly to the gas space while the outlet gas along with the excess medium uniformly passing through the matrix of carriers 9b, entering said tube 3c and exiting from the outlet end and port 3b. The fresh or recirculated medium or cells enters from port 5 and passes through the carrier 9b which acts as a filter to entrap and retain the suspension cells on said carriers 9b or for adherent cells to attach and form an immobilized cell packed bed. Said culture vessel 1 also comprises of a baffle 2 as described in other systems described above for good mixing and oxygenation at low rocking speed for little to no shear stress. The liquid volume is maintained at constant level 7 around the gas outlet port 3b, which is about half the volume of said vessel. The diameter of said compartment 9a can be in any size depending on the desired ratio of total cell number to medium volume. The higher cell density is a result of the increased loading of carriers which creates internal change of nutrient concentration and increases the nutrient consumption rate. Accordingly, it would require higher dilution rate or fresh medium feeding rate to compensate for this internal change and to perform this single pass perfusion culture. Alternatively a medium reservoir in the reservoir assembly is used to circulate the medium that is in said vessel 1 so that the medium concentration change in said vessel is more subtle.

Figure 15:
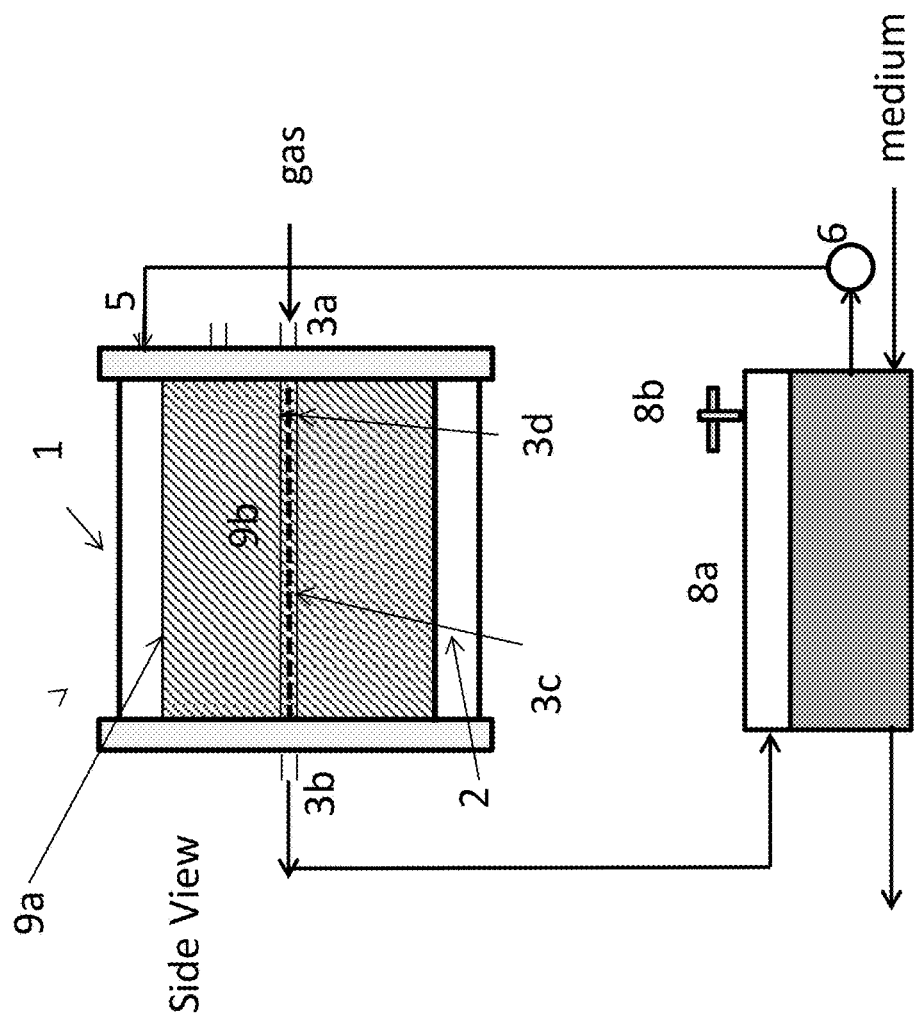
FIG. 15 shows the schematic diagram of the perfusion culture using the bioreactor system shown in FIG. 14A in conjunction with a medium reservoir and having the medium circulated between both vessels according to the present invention.

In FIG. 15 is shown the schematic diagram of the perfusion culture using said bioreactor system shown in FIG. 14A but in conjunction with a medium reservoir 8a where medium circulates between both vessels by a pump 6. Said medium reservoir 8a has an exit vent filter 8b and is equipped with pH, DO sensors and controller, and also an agitation mechanism such as agitator or shaker. For performing a perfusion culture a separate pump 6 is used to feed in the fresh medium at a desirable perfusion rate and to also remove the medium from the reservoir 8a at the same rate while the medium exiting from port 3b of culture vessel 1 recirculates through the reservoir 8a and returns to port 5 at a gentle slow rate. All suspension or adherent cells remaining suspension in the medium are retained in the carriers while flowing through the matrix in the one directional flow.

Another embodiment as described is a bioreactor system comprising:

a) one vessel assembly comprising at least one closed tubular flexible culture vessel and at least one open tubular rigid supporting vessel; wherein said supporting vessel comprises at least one tube and two closed ends made of rigid single use or reusable material; wherein said supporting vessel lies along its longitudinal axis and configured to hold and support a flexible culture vessel inside of said supporting vessel; wherein said supporting vessel comprising at least one baffle; wherein the baffle is attached to or tightly close to all inside contact surface of said supporting vessel; and wherein the baffle has a ratio of greater than 0.1 and less than 0.9 of heights of said baffle to the cross-sectional surface perpendicular to the longitudinal axis of said supporting vessel; wherein at least one closed tubular culture vessel made of flexible single use material as a bag wherein said bag has the size and shape allowing for close nesting into said one supporting vessel so that said bag closely contacts the entire internal contacting surface of said supporting vessel as the bag is inflated; wherein said culture vessel comprises at least one media port configured to allow culture material to flow in and out of said culture vessel; and wherein said culture vessel comprises at least one set of two gas ports configured to allow the respiratory gas to flow in and out of said culture vessel;

b) one reservoir assembly comprising at least one closed container made of single use or reusable material;

b) one pumping apparatus fluidly coupled to at least one media port of said culture vessel and configured to pump culture material in and out of said culture vessel through said at least one port;

c) one gassing apparatus coupled to at least one set of two gas ports of said culture vessel and configured to passing the gas in through one gas port and out of said culture vessel through another gas port;

d) one gas blending apparatus coupled to said gassing apparatus and configure to blend the gases including oxygen, nitrogen, carbon dioxide, air and the like;

e) one rocking apparatus configured to hold and position said supporting vessel and rock about the longitudinal axis along the plane perpendicular to said axis at angle of less than 360 degrees;

f) one monitoring apparatus configured to monitor one or more parameters of said vessel assembly, said reservoir assembly, said pumping apparatus, said gassing apparatus, and said gas blending apparatus and said rocking apparatus;

g) one control apparatus connected wired or wirelessly to vessel assembly, said reservoir assembly, said pumping apparatus, said gassing apparatus, said gas blending apparatus, said rocking apparatus and said monitoring apparatus wherein said control apparatus is configured and programmed to coordinate the positioning and movement of said vessel assembly using said rocking apparatus with the pumping culture material in and out of said culture vessel using said pumping apparatus, the passing respiratory gases to enter and exit said culture vessel through one set of inlet/outlet ports and remaining in gas space at all times using the gassing apparatus; to adjust the gas concentration using said gas blending apparatus; and to control the operating parameters of said vessel assembly monitored by said monitoring apparatus; and/or h) at least one compartment confined inside of said flexible culture vessel bag to hold carriers as a fixed packed bed for adherent cell cultures.

Disclosed herein are bioreactor systems comprising a vessel assembly, a reservoir assembly a pumping apparatus, a gassing apparatus, a gas blending apparatus, a rocking apparatus, a monitoring apparatus, and a control apparatus.

As disclosed herein said bioreactor system comprises one vessel assembly. Said vessel assembly comprises at least one closed tubular flexible culture vessel and at least one open tubular rigid supporting vessel.

As disclosed herein said open tubular supporting vessel comprises at least one tube and two end plates referred to as head plates bolted together but without seal between the tube and head plates. The tubing of the culture vessel freely goes through the openings on the head plates. The culture vessel is inserted inside of the supporting vessel and connected to the external containers of the reservoir assembly. Said vessel is made of reusable material including stainless steel or glass or the like, or of single use rigid material including polymeric material or the like. Said polymeric material includes polystyrene, polymethylmethacrylate, polyvinyl chloride, polycarbonate, polyesters, polyamides, polyethylene, polypropylene or the like. Said tube of vessel is most commonly in circular, oval and square shapes but also in any other polygonal shapes with many sides including but not limited to 3, 4, 5, and 6. Said supporting vessel comprises at least one baffle contacts surface of said supporting vessel, having a ratio of greater than 0.1 and less than 0.9 of heights of said baffle to the cross-sectional surface perpendicular to the horizontal longitudinal axis of said supporting vessel. For a circular tubular vessel, for example, the ratio of the heights of said baffle to the cross-sectional surface of said vessel perpendicular to the longitudinal axis is the ratio of baffle height to the diameter of circular vessel. Preferably the ratio is 0.45 to 0.75. As used herein, "contacts" refers to any means by which one component is caused to touch or be held in close proximity to, but not necessarily directly touching or touching along the entire adjacent surface of another component (e.g., the baffle and the interior surface of the culture vessel). It is understood and herein contemplated that the when an component such as, for example, a baffle, is in contact with another component such as, for example, the inside wall or ends of a culture vessel, the contact can refer to physical touching or merely close proximity such that the desired function can still be maintained. It is further understood that the contact can comprise sealingly engaging one component to the other (e.g., the baffle to the inside of the culture vessel) or attachment at one or more desired locations. The contact can be achieved through the use of an epoxy, glue, tape adhesive, friction, mechanical pressure, tracks, surface tension, screws, rivets, nails, stables, or the like or any combination thereof. It is understood and herein contemplated that for the function of a component (e.g., a baffle) that is contact to another component to occur, there may be instances where direct physical contact is intermittent or incomplete, such as when physical contact is maintained through mechanical attachment in a few areas allowing for space to occur between the components between points of mechanical attachment. In such instances, contact is deemed to have been maintained so long as the functional properties are maintained. Thus, where the first component (such as, for example, a baffle) is held in close proximity to the second component (such as, for example, the interior of the culture vessel) or attached in certain areas but not sealingly engaging along the entirety length of the adjacent surfaces, the contact is still achieved. Said baffle can be in various shapes and configurations including flat, curved, angled and helical or the like and attached or positioned tightly close to all internal contact walls of tube and head plates along the longitudinal axis of said supporting vessel to assure well mixing of culture material inside of the inserted flexible culture vessel even at a slow rocking rate.

As disclosed herein said at least one closed tubular culture vessel is made of flexible single use material as a bag wherein said bag has the size and shape allowing for close nesting into said one supporting vessel so that said bag closely contacts the entire internal contacting surface of said supporting vessel as the bag is inflated; said culture vessel has the size and shape allowing for close nesting into said supporting vessel so that said bag closely contacts the entire internal contacting surface of said supporting vessel as the bag is inflated; said tubular culture vessel bag comprises of one flexible tube and sealed with the same material on the two closed ends to form a closed three dimensional (3D) flexible vessel bag. Said flexible vessel bag is made of single use material including polymeric material including polyvinyl acetate, polypropylene, polyvinyl chloride, polyethylene terephthalate or the like. Said tube of vessel is most commonly in circular, oval and square shapes but also in any other polygonal shapes with many sides including but not limited to 3, 4, 5, and 6.

As disclosed herein said culture vessel bag is a closed system wherein said culture vessel bag is connected with only tubing between the inside and outside of said vessel bag to perform the exchange of culture medium and cells through non-invasive valves or pumps during the entire operation so that there is no culture liquid inside of said vessel bag that is ever open directly to the external environment through human intervention.

Said culture vessel is configured to lie and rock said entire vessel along the longitudinal axis at speed of less than 5 rpm without using agitator. Most common bioreactors stand vertically along the latitudinal axis perpendicular to the ground plane and require at least one agitator with speed of greater than 50 rpm which generates high shear stress. For equivalent mixing effectiveness said horizontally rocked vessel generates significantly less shear stress. Furthermore, said horizontally rock culture vessel requires no mechanical seal and motor, making the construction of said vessel simpler and economical.

As disclosed herein said bioreactor system comprises one reservoir assembly wherein said assembly comprising at least one closed container made of single use or reusable material. Said container are for storage of fresh medium, spent medium, culture material from said culture vessel, inoculum, or the like or for retaining of exhaust gas, etc. Said container is made of single use material including polymeric material or the like as a bag, bottle, tank, etc. or of reusable material including glass, stainless steel etc. Each of said container comprises at least one vent with air filter and at least one port.

As disclosed herein said bioreactor system comprises a pumping apparatus coupled to at least one medium port configured to allow fluidic culture material to flow in and out of at least one cell culture vessel; said pumping apparatus contains at least one pump to transport the fluid in and out the vessel. Ideally the pump is a peristaltic pump or the like which has no part that contacts the fluid to maintain system integrity. Said fluidic culture material can be inoculum, fresh medium, spent medium, seeded medium, virus solution, enzymatic reagents, etc.

As disclosed herein, said at least one culture vessel comprising at least one set of two gas ports including but not limited to 1, 2 and 3 sets wherein each gas port is connected with a tubing and a pinch valve and configured to couple with a gassing apparatus and a control apparatus to regulate the respiratory gas entering through one gas port and out of said culture vessel through another gas port one set at a time to always maintain the gas flow is in the gas space. Said respiratory gas is a gas mixture required for cells to cultivate under various desirable concentration of oxygen, carbon dioxide or the like. Said gassing apparatus is to supply the gas by a gas pump or a pressurized gas cylinder; and for monitoring. Said monitoring apparatus is to monitor the flow rate by a rotameter or mass flow meter and coupled to the control apparatus to control the flow rate by mass flow controller.

As disclosed herein said bioreactor system comprises a gas blending apparatus to alter the gas composition by adjusting the flow rate of each supplied gas using a mass flow controller and controlled by a control apparatus or regulated manually by a rotameter. Said gas blending apparatus is a manifold to combine the supplied gases including air, oxygen, nitrogen and $CO_2$ or the like in a given percent purity to generate a desired concentration of a gas mixture for respiration of said cell culture. Commonly, each of said gas supplies is in a gas cylinder with 100% purity except the air which is supplied by an air pump.

As disclosed herein said bioreactor system comprises one rocking apparatus configured to hold and position said at least one culture vessel; said rocking apparatus is driven by a DC stepping motor that moves in discrete steps. Said motor has multiple coils which are organized in groups named "phases". By energizing each phase in sequence, the motor rotates one step at a time. With computer-controlled stepping, a very precise positioning and/or speed control is achieved. Other options available for positioning control depend on the type of actuator driving the system. An actuator is a mechanical device that moves or controls a specific element or a series of elements within a system. The actuators include stepping motor, pneumatic, brake motor, clutch brake, DC servo system and AC servo system or the like. Said culture vessel is coupled to the shaft of said motor directly or through a driven chain including belt and chain and the like. Said rocker is configured to rock said at least one cell culture vessel about the longitudinal axis along the plane perpendicular to said axis at any angle of less than 360 degrees and at any rocking rate of less than 30 rpm, preferably at angle of less than 180 degrees and rocking rate of less than 5 rpm, and to hold at any angle for any length of time. With this moving flexibility and relative small footprint said system is capable of performing seeding, culturing, medium exchange, cell detachment and harvesting all in one place and in one closed vessel.

As disclosed herein said bioreactor system comprises one monitoring apparatus configured to monitor one or more parameters of culture material in said vessel assembly, reservoir assembly, pumping apparatus, gassing apparatus, gas blending and rocking apparatus. Said parameters of said culture vessel and culture material of said culture vessel include all biophysical, biochemical and biological properties such as temperature, pH, pressure, dissolved oxygen (DO), dissolved carbon dioxide (DCO2), glucose, lactate, glutamine, glutamate, ammonium, pH, sodium, potassium, osmolality, protein, nucleic acid, total cell number, cell viability, cell morphology and the like. Said parameters are monitored using sensors, biosensors, imaging devices, on-line or off-line biochemical or biophysical analyzers or the like. In said vessel assembly and reservoir assembly the pressure for system integrity and filter blockage using the pressure sensor is monitored.

In said pumping apparatus pumping rate is monitored using the shaft rotating speed of said peristaltic pump. In said gassing apparatus and gas blending apparatus the flow rates of each gas is monitored using mass flow meter. In said rocking apparatus its rocking angle, position and rate using the stepping motor or the like is monitored.

As disclosed herein said bioreactor system comprises a control apparatus wherein said control apparatus may include one or more computing devices capable of processing data; microprocessors, programmable logic arrays, data storage, input devices, output device; human machine interface (HMI) and programmable logic control (PLC) etc. Said control apparatus is configured to connect wired or wirelessly to each element of said bioreactor system including said vessel assembly, said reservoir assembly, said pumping apparatus, said gassing apparatus, gas blending apparatus, rocking apparatus and monitoring apparatus and the like. Said control apparatus is configured and programmed to coordinate the positioning and movement of said culture vessel using said rocking apparatus with the culture material pumping in and out of at least one cell culture vessel using said pumping apparatus, the control of the passing respiratory gas in and out of said culture vessel using said gassing apparatus, to adjust the gas composition and gas flow rate using said gassing and blending apparatus and to control the operating parameters of said vessel assembly including temperature, pH, DO, pressure, glucose or the like monitored by said monitoring apparatus. Said control apparatus controls the on/off of each pinch valve to regulate the gas flow through each set of gas inlet and outlet ports to permit the gas flow pattern during the rocking motion to always maintain the gas flow above the liquid phase. In such a manner the liquid volume or loading capacity of said vessel can be significantly increased by at least 40-50% compared to using only one single set. It also mitigates the foaming problem because the gas flow always remains only in the gas phase. Said control apparatus described herein provides a fully automated solution to accomplish one or more processes including seeding, culturing, medium exchange, cell detaching and harvesting cells from said culture vessel.

As disclosed herein said culture vessel has at least one compartment confined inside of said vessel by a screen or perforated plate to hold carriers as a fixed packed bed for adherent cell cultures. Said carriers are 2D non-porous flat or curved surface or 3D porous surface carriers or scaffolds. A 2D carrier such as that made of polystyrene or the like material is a non-porous surface for cells to attach and form monolayer culture. A 3D porous carrier or scaffold such as that made of glass beads, ceramic, polyester fibers, polyurethane fibers or the like material has a porous surface for cells to attach and to form three dimensional multilayer cultures. Both carriers are commonly treated with plasma to change the surface properties to improve adhesion. If these carriers are loosely-held individuals, they are packed as a bed by a perforated plate or a screen secured to said vessel. The flexibility of rocking motion of said culture vessel with a packed bed of carriers inside of said compartment permits the carriers to alternately expose the cells directly to gas space for oxygenation and submerge the cells to the medium for nutrient replenishment. This disclosure provides the most efficient oxygenation while requiring little to no shear stress to accommodate the extra demand of oxygen for the high cell density culture.

In FIG. 12 is illustrated an opened double tube horizontal supporting vessel 18 comprising a double tube with outer tube 11 and inner tube 10, two head plates 1a and 1b with no closed culture vessel bag 1 inserted inside. Both head plates 1a, 1b and tube 10, 11 are bolted together but the openings on the head plates are open. Said supporting vessel 18 is to be used to hold the single use culture vessel bag 1 inside and let said bag closely contact to the inner supporting vessel tube 10, two head plates 1a, 1b and the baffle 2 when said bag 1 is inflated. The front view shows the opening ports 3a and 4a of head plate 1a which are to hold two gas inlet tubing 3x, 4x of said culture vessel bags shown in FIG. 13(A) and FIG. 13(B); opening ports 5a/b/c for feeding tubing 5x/y/z of said culture bags 1; and openings 6x/y for sensors 6a/b inserted in the bags, and baffle 2 fit to the deeply dented surface 2z of the culture vessel 1. The side view shows the baffle 2 and the space between the two tubes 10 and 11 that serves as a jacket for heating or cooling water pumping through ports 8a and circulates in said space to control the temperature of the culture vessel 1 which is in close contact to the jacketed walls. The rear view shows the rear head plate 1b with opening ports 3b and 4b to hold the gas outlet tubing 3y and 4y of the culture bag 1 shown in FIG. 13(A) and FIG. 13(B).

In FIG. 13(A) is illustrated a disposable cylindrical three dimensional (3D) culture vessel 1 with front, side, and rear views. In FIG. 13(B) is illustrated a disposable cylindrical 3D culture vessel bag 1 with one carrier compartment 9a in front, side, and rear views. The front view of FIG. 13(A) shows that the front side of said 3D bag 1 has a deeply dented surface 2z which is tightly fit to the large rigid baffle 2 of said rigid supporting vessel 18 as shown in FIG. 12 when said vessel bag 1 is inserted to said supporting vessel 18 and inflated; tubing 3x, 4x for inlets of gas, tubing 5x/y for feeding of medium or the like; and sensors 6a/b. The side view of FIG. 13(A) shows said bag 1 with dented surface 2z, sensors 6a/6b and gas inlet/outlet tubing 3x/y and 4x/y. The rear view of FIG. 13(A) shows the rear side of said 3D bag 1 with a deeply dented surface 2z, tubing 3b, and 4b for outlets of gas. The front, side and rear views of FIG. 13(B) are the same as those of FIG. 13(A) but with one carrier compartment 9a enclosed by a screen or perforated film 8 and a cap 10a for sampling, filling or removing of the carriers.

As disclosed herein said culture vessel bag wherein said compartment of carriers enclosed by a screen or perforated film is situated in the center of said culture vessel bag and said gas inlet and one outlet are situated in the center of the horizontal axis in both ends of said compartment and said vessel. For suspension cells the perfusion culture is able to use the packed bed of carriers as a filter to entrap and retain the cells inside of the culture vessel or bag without the requirement of another cell retaining device. Said bioreactor system accomplishes this objective by having the culture material along with the respiratory gas enter into said vessel through the bed of carriers to retain the cells and to allow the medium exiting from the center of said vessel while the volume remains constant inside of said vessel. The volume of medium in said culture vessel 1 is about half of the total vessel volume. The inlet gas enters from the center of one end of vessel and exits through another end along with the exiting medium in such that the gas remains above the liquid phase and mitigates the foaming problem. The rocking motion of the carrier compartment also allows the imbedded cells in the carriers to alternately expose to gas and submerge to liquid phases to achieve the best oxygenation.

Figure 14B:
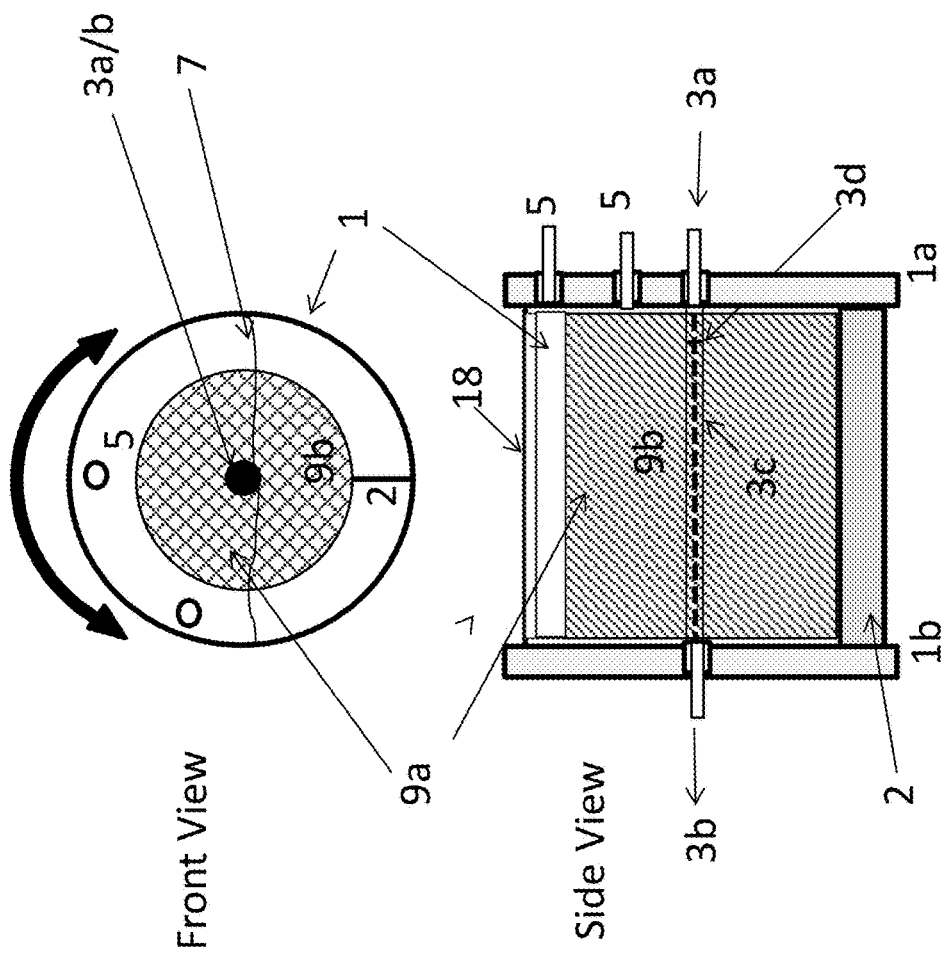
FIG. 14B shows the front view of a closed culture vessel bag wherein its carrier compartment enclosed by a perforated tube is situated in the center of the culture vessel bag along the horizontal axis and side view of an open supporting vessel to hold the closed culture vessel bag inside according to the present invention.

In FIG. 14B is illustrated the front and side views of said culture vessel 1 wherein said culture vessel 1 is flexible and made of single use material as a bag. Said culture vessel 1 comprises a carrier compartment 9a which is situated in the center of said culture vessel 1 and a perforated tube 3c situated in the center along the horizontal axis with only one gas inlet 3a and one outlet 3b in each end of said tube 3c and has a partition 3d in said tube 3c toward the inlet end so that the inlet gas diffuses quickly to the gas space while the outlet gas along with the excess medium uniformly passing through the matrix of carriers 9b, entering said tube 3c and exiting from the outlet end and port 3b. The fresh or recirculated medium or cells enters from port 5 and passes through the carrier 9b which acts as a filter to entrap and retain the suspension cells on said carriers 9b or for adherent cells to attach and form an immobilized cell packed bed. Said culture vessel 1 is inserted in an open supporting vessel 18 with opening in both head plates 1a and 1b to hold said gas and medium tubing 3a,3b, 5. Said supporting vessel 18 also comprises of a baffle 2 as described with reference to FIG. 12 for good mixing and oxygenation at low rocking speed for little to no shear stress. Said culture vessel 1 comprises a deeply dented surface to tightly attach said baffle 2 as the vessel bag 1 is inflated. The liquid volume is maintained at constant level 7 around the gas outlet port 3b, which is about half the volume of said vessel. The diameter of said compartment 9a can be in any size depending on the desired ratio of total cell number to medium volume. The higher cell density is a result of the increased loading of carriers which creates internal change of nutrient concentration and increases the nutrient consumption rate. Accordingly, it would require higher dilution rate or fresh medium feeding rate to compensate for this internal change and to perform this single pass perfusion culture. Alternatively a medium reservoir in the reservoir assembly is used to circulate the medium that is in said vessel 1 so that the medium concentration change in said vessel is more subtle.

What is claimed is:

1. A bioreactor system, comprising:
a vessel assembly comprising:
a tube positioned to lie along a longitudinal axis, the tube having ends;
a baffle extending within the tube, the baffle extending along and contacting an inner wall of the tube along the longitudinal axis and extending to and contacting the ends of the tube, wherein a ratio of a major surface area of the baffle to a central cross-sectional area of the tube along the longitudinal axis is greater than about 0.45 and less than about 0.90;
at least one media port to allow culture material to flow into or out of the vessel assembly; and
a plurality of gas ports to allow to allow gas to flow into or out of the vessel assembly;
a rocking apparatus configured to rock the vessel assembly about the longitudinal axis in a rocking sequence, the rocking sequence comprising rotating the vessel assembly about the longitudinal axis in a first direction less than 360 degrees and rotating the vessel assembly about the longitudinal axis in a second direction less than 360 degrees; and
a gassing apparatus configured to flow gas through one of the plurality of gas ports during a first portion of the rocking sequence and to alternately flow gas through another one of the gas ports during a second portion of the rocking sequence.

2. The bioreactor system of claim 1, wherein:
the ends of the tube are closed ends such that the tube and the ends form as a culture vessel; and
the baffle extends along and attaches sealingly to an inner wall of the tube along the longitudinal axis and extends and attaches sealingly to the ends of the tube.

3. The bioreactor system of claim 1, wherein:
the vessel assembly further comprises a closed flexible culture vessel bag supported within the tube; and
the closed flexible culture vessel bag comprises at least one bag port to allow culture material or gas to flow into or out of the closed flexible culture vessel bag.

4. The bioreactor system of claim 3, wherein:
the at least one bag port comprises a plurality of bag ports; and
the gassing apparatus is configured to flow gas through one of the plurality of bag ports during the first portion of the rocking sequence and to alternately flow gas through another one of the plurality of bag ports during the second portion of the rocking sequence.

5. The bioreactor system of claim 4, wherein the closed flexible culture vessel bag comprises a deep dent surface to fit around the baffle when the closed flexible culture vessel bag is inflated.

6. The bioreactor system of claim 2, wherein:
the culture vessel further comprises at least one compartment for at least one carrier for cells to attach and grow;
the at least one carrier comprises at least one of a two-dimensional (2D) carrier and a three-dimensional (3D) carrier;
the 2D carrier comprises at least one of a flat or curved non-porous carrier for cells to attach and form a monolayer culture; and
the 3D carrier comprises at least one of a porous glass bead, ceramic, or fiber carrier for cells to attach and form a 3D multilayer culture.

7. The bioreactor system of claim 6, wherein:
the at least one compartment is located in a center of the culture vessel along the longitudinal axis of the culture vessel.

8. The bioreactor system of claim 3, wherein:
the closed flexible culture vessel bag further comprises at least one compartment for at least one carrier for cells to attach and grow;
the at least one carrier comprises at least one of a two-dimensional (2D) carrier and a three-dimensional (3D) carrier;
the 2D carrier comprises at least one of a flat or curved non-porous carrier for cells to attach and form a monolayer culture; and
the 3D carrier comprises at least one of a porous glass bead, ceramic, or fiber carrier for cells to attach and form a 3D multilayer culture.

9. The bioreactor system of claim 8, wherein:
the compartment is located in a center of the closed flexible culture vessel bag along the longitudinal axis.

10. The bioreactor system of claim 1, further comprising:
a pumping apparatus configured to pump culture material into and out of the at least one media port;
a monitoring apparatus configured to monitor one or more parameters of at least one of the vessel assembly, the rocking apparatus, the pumping apparatus, and the gassing apparatus; and a control apparatus configured to coordinate at least one operation of at least one of the rocking apparatus, the pumping apparatus, and the gassing apparatus based on the one or more parameters.

11. A bioreactor system, comprising:
a vessel assembly comprising:
  a tube positioned to lie along a longitudinal axis, the tube having ends;
  a baffle extending within the tube, the baffle extending along and contacting an inner wall of the tube along the longitudinal axis and extending to and contacting the ends of the tube, wherein a ratio of a major surface area of the baffle to a central cross-sectional area of the tube along the longitudinal axis is greater than about 0.45 and less than about 0.90;
  at least one media port to allow culture material to flow into or out of the vessel assembly;
  a plurality of gas ports to allow to allow gas to flow into or out of the vessel assembly;
a rocking apparatus configured to rock the vessel assembly about the longitudinal axis in a rocking sequence, the rocking sequence comprising rotating the vessel assembly about the longitudinal axis in a first direction less than 360 degrees and rotating the vessel assembly about the longitudinal axis in a second direction less than 360 degrees;
a gassing apparatus configured to flow gas through one of the plurality of gas ports during a first portion of the rocking sequence and to alternately flow gas through another one of the gas ports during a second portion of the rocking sequence;
a pumping apparatus configured to pump culture material into and out of the at least one opening;
a monitoring apparatus configured to monitor one or more parameters of at least one of the vessel assembly, the rocking apparatus, the gassing apparatus, and the pumping apparatus; and
a control apparatus configured to coordinate at least one operation of at least one of the vessel assembly, the rocking apparatus, the pumping apparatus, and the gassing apparatus based on the one or more parameters.

12. The bioreactor system of claim 11, wherein:
the ends of the tube are closed ends such that the tube and the ends form as a culture vessel; and
the baffle extends along and attaches sealingly to an inner wall of the tube along the longitudinal axis and extends and attaches sealingly to the ends of the tube.

13. The bioreactor system of claim 12, wherein:
the culture vessel further comprises at least one compartment for at least one carrier for cells to attach and grow;
the at least one carrier comprises at least one of a two-dimensional (2D) carrier and a three-dimensional (3D) carrier;
the 2D carrier comprises at least one of a flat or curved non-porous carrier for cells to attach and form a monolayer culture; and
the 3D carrier comprises at least one of a porous glass bead, ceramic, or fiber carrier for cells to attach and form a 3D multilayer culture.

14. The bioreactor system of claim 13, wherein:
the compartment is located in a center of the culture vessel along the longitudinal axis of the culture vessel.

15. The bioreactor system of claim 11, wherein:
the vessel assembly further comprises a closed flexible culture vessel bag supported within the tube; and
the closed flexible culture vessel bag comprises at least one bag port to allow culture material or gas to flow into or out of the closed flexible culture vessel bag.

16. The bioreactor system of claim 15, wherein:
the at least one bag port comprises a plurality of bag ports; and
the gassing apparatus is configured to flow gas through one of the plurality of bag ports during the first portion of the rocking sequence and to alternately flow gas through another one of the plurality of bag ports during the second portion of the rocking sequence.

17. The bioreactor system of claim 15, wherein:
the closed flexible culture vessel bag comprises at least one compartment for at least one carrier for cells to attach and grow;
the at least one carrier comprises at least one of a two-dimensional (2D) carrier and a three-dimensional (3D) carrier;
the 2D carrier comprises at least one of a flat or curved non-porous carrier for cells to attach and form a monolayer culture; and
the 3D carrier comprises at least one of a porous glass bead, ceramic, or fiber carrier for cells to attach and form a 3D multilayer culture.

18. The bioreactor system of claim 17, wherein:
the at least one compartment is located in a center of the closed flexible culture vessel bag along the longitudinal axis.

19. The bioreactor system of claim 11, wherein:
the control apparatus is connected wired or wirelessly to the vessel assembly, the pumping apparatus, the gassing apparatus, the rocking apparatus, and the monitoring apparatus, and
the control apparatus is configured to:
  coordinate positioning and movement of the vessel assembly using the rocking apparatus with culture material pumping in and out of the vessel using the pumping apparatus;
  coordinate positioning and movement of carriers to alternately expose the carriers to liquid and gas phases for nutrient replenishment and oxygenation using the rocking apparatus;
  pass respiratory gases to enter and exit the vessel through the plurality of gas ports in gas space at all times using the gassing apparatus; and
  control operating parameters of the vessel assembly based on the one or more parameters monitored by the monitoring apparatus.

* * * * *